US012381228B2

(12) United States Patent
 Viavattine

(10) Patent No.: US 12,381,228 B2
(45) Date of Patent: Aug. 5, 2025

(54) BATTERY ASSEMBLY FOR MEDICAL DEVICE

(71) Applicant: Medtronic, Inc., Minneapolis, MN (US)

(72) Inventor: Joseph J. Viavattine, Vadnais Heights, MN (US)

(73) Assignee: Medtronic, Inc., Minneapolis, MN (US)

( * ) Notice: Subject to any disclaimer, the term of this patent is extended or adjusted under 35 U.S.C. 154(b) by 514 days.

(21) Appl. No.: 17/116,305

(22) Filed: Dec. 9, 2020

(65) Prior Publication Data

US 2021/0202952 A1    Jul. 1, 2021

Related U.S. Application Data

(60) Provisional application No. 62/955,725, filed on Dec. 31, 2019.

(51) Int. Cl.
 *H01M 4/66* (2006.01)
 *H01M 50/209* (2021.01)

(52) U.S. Cl.
 CPC ........... *H01M 4/66* (2013.01); *H01M 50/209* (2021.01); *H01M 2220/30* (2013.01)

(58) Field of Classification Search
 CPC ........ H01M 4/66; H01M 4/70; H01M 50/209; H01M 10/0436; H01M 10/0585
 See application file for complete search history.

(56) References Cited

U.S. PATENT DOCUMENTS

| 4,204,036 A | * | 5/1980 | Cohen ............... H01M 6/48 429/152 |
| 5,147,737 A | | 9/1992 | Post et al. |
| 6,933,074 B2 | | 8/2005 | Frustaci et al. |

(Continued)

FOREIGN PATENT DOCUMENTS

| CN | 103959515 A | 7/2014 |
| CN | 104011929 A | 8/2014 |
| CN | 109417135 A | 3/2019 |

OTHER PUBLICATIONS

International Search Report and Written Opinion of International Application No. PCT/US2020/064402, mailed Mar. 15, 2021, 11 pp.

(Continued)

*Primary Examiner* — Jonathan G Leong
*Assistant Examiner* — Katharine A Caughron
(74) *Attorney, Agent, or Firm* — Shumaker & Sieffert, P.A.

(57) ABSTRACT

In some example, a battery assembly for an implantable medical device includes a first anode plate comprising a first anode current collector and a first active material on the first anode current collector; a second anode plate comprising a second anode current collector and a second active material on the second anode current collector; and a cathode plate between the first anode plate and the second anode plate, wherein the cathode plate comprises a cathode current collector, the cathode current collector having an exposed portion, wherein the first active material is recessed relative to the exposed portion of the cathode plate such that a first nearest perimeter of the first active material is further from the exposed portion of the cathode current collector compared to a second nearest perimeter of the second active material.

9 Claims, 25 Drawing Sheets

(56) References Cited

U.S. PATENT DOCUMENTS

| | | | |
|---|---|---|---|
| 7,035,078 B1* | 4/2006 | Viavattine | H01M 50/54 |
| | | | 361/303 |
| 7,592,097 B2 | 9/2009 | Urso et al. | |
| 9,431,679 B2 | 8/2016 | Kwon et al. | |
| 10,026,994 B2 | 7/2018 | Kwon et al. | |
| 10,727,454 B2 | 7/2020 | Bruch et al. | |
| 2004/0127952 A1* | 7/2004 | O'Phelan | H01M 50/107 |
| | | | 607/36 |
| 2007/0202401 A1* | 8/2007 | Viavattine | H01M 4/382 |
| | | | 429/209 |
| 2013/0131744 A1 | 5/2013 | Viavattine | |
| 2013/0131745 A1 | 5/2013 | Viavattine | |
| 2014/0050958 A1* | 2/2014 | Kwon | H01M 10/0587 |
| | | | 429/94 |
| 2015/0086842 A1* | 3/2015 | Kang | H01M 50/10 |
| | | | 429/156 |
| 2017/0317331 A1 | 11/2017 | Vedoy | |
| 2018/0083255 A1* | 3/2018 | Kim | H01M 50/105 |
| 2019/0131591 A1 | 5/2019 | Beauvais et al. | |

OTHER PUBLICATIONS

First Office Action and Search Report, and translation thereof, from counterpart Chinese Application No. 202080090915.X dated Sep. 20, 2024, 16 pp.

* cited by examiner

BATTERY ASSEMBLY FOR MEDICAL DEVICE

This application claims the benefit of U.S. Provisional Patent Application No. 62/955,725, filed on Dec. 31, 2019, the entire content of which is incorporated herein by reference.

TECHNICAL FIELD

The disclosure relates to batteries, such as, batteries for use in medical devices.

BACKGROUND

Medical devices such as implantable medical devices (IMDs) include a variety of devices that deliver therapy (such as electrical simulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or to power circuitry for monitoring a physiological parameter of a patient and controlling the functionality of the medical device.

SUMMARY

In some aspects, the disclosure is directed to battery assemblies for use, e.g., in a medical device, and techniques for manufacturing battery assemblies. As described in further detail below, battery assemblies may have one or more cathodes having recessed active material and/or one or more anodes having recessed active material. In some examples, the recessed active material of the anode may be recessed relative to an exposed portion (e.g., a tab) of a current collector of an adjacent cathode. In some examples, the recessed active material of the cathode may be recessed relative to a tab (e.g., the edge of the tab) of a current collector of an adjacent anode. Example battery assemblies may have stacked plate design including a plurality of electrode plates are described although other battery assembly designs are contemplated.

In one example, the disclosure is directed to a battery assembly comprising a first anode plate comprising a first anode current collector and a first active material on the first anode current collector; a second anode plate comprising a second anode current collector and a second active material on the second anode current collector; and a cathode plate between the first anode plate and the second anode plate, wherein the cathode plate comprises a cathode current collector, the cathode current collector having an exposed portion, wherein the first active material is recessed relative to the exposed portion of the cathode plate such that a first nearest perimeter of the first active material is further from the exposed portion of the cathode current collector compared to a second nearest perimeter of the second active material.

In another example, the disclosure is directed to a method for forming a battery assembly, the method comprising assembling an electrode stack, the electrode stack comprising: a first anode plate comprising a first anode current collector and a first active material on the first anode current collector; a second anode plate comprising a second anode current collector and a second active material on the second anode current collector; and a cathode plate between the first anode plate and the second anode plate, wherein the cathode plate comprises a cathode current collector, the cathode current collector having an exposed portion, wherein the first active material is recessed relative to the exposed portion of the cathode plate such that a first nearest perimeter of the first active material is further from the exposed portion of the cathode current collector compared to a second nearest perimeter of the second active material.

In another example, the disclosure is directed to a battery assembly comprising an anode plate comprising an anode current collector and a first active material on the anode current collector, the anode current collector having a tab portion; and a cathode plate adjacent the anode plate, the cathode plate comprising a cathode current collector and second active material, wherein the second active material comprises a recessed portion, the recessed portion being recessed relative to the tab portion of the first anode current collector.

In another example, the disclosure is directed to a method for forming a battery assembly, the method comprising assembling an electrode stack, the electrode stack comprising a first anode plate comprising a first anode current collector and a first active material on the first anode current collector, the first anode current collector having a first exposed portion; a second anode plate comprising a second anode current collector and a second active material on the second anode current collector, the second anode current collector having a second exposed portion; a cathode plate between the first anode plate and the second anode plate, wherein the cathode plate comprises a cathode current collector, wherein the cathode current collector is recessed relative to the first exposed portion of the first anode current collector and the second exposed portion of the second current collector.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
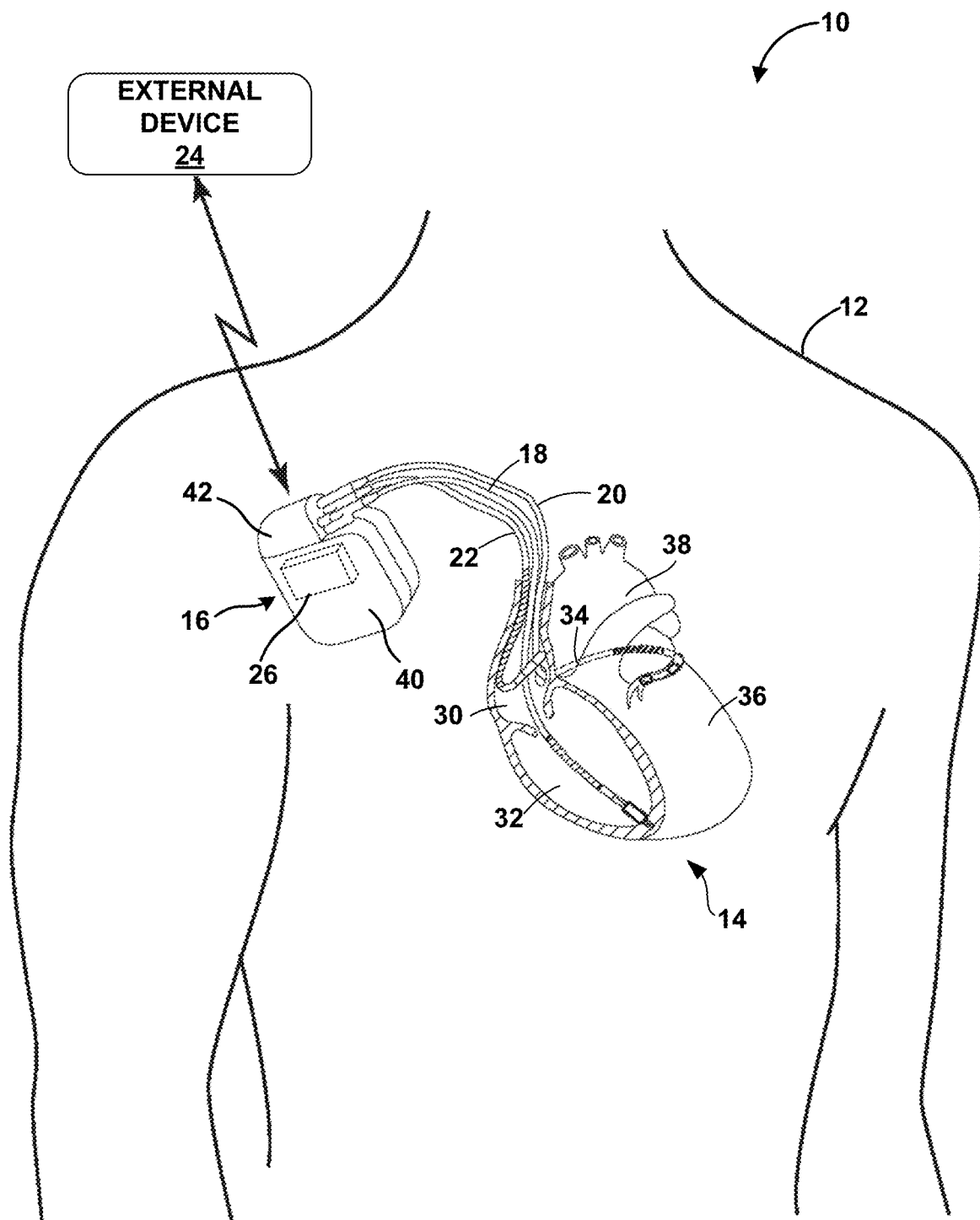
FIG. 1 is a conceptual diagram that illustrates an example medical device system that may be used to deliver therapy to a patient.

A variety of medical devices may utilize one or more batteries as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to batteries employed in IMDs that provide cardiac rhythm management therapy. However, as will be apparent from the description herein, examples of the disclosure are not limited to IMDs that provide such therapy. For example, in some instances, one or more of the example batteries described herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example batteries of this disclosure may be employed in medical devices configured to monitor one or more patient physiological parameters, e.g., by monitoring electrical signals of the patient, alone or in conjunction with the delivery of therapy to the patient. In still other examples, batteries of the disclosure may be employed as a power source in devices other than medical devices.

In some examples, a battery of an IMD may include a plurality of electrode plates (e.g., including both anode and cathode plates) stacked on each other in which each of the plates includes a tab extending therefrom. The tabs of the anode plates may be aligned with each other in a stack and electrically connected to each other to collectively form an anode of the battery. In this sense, the tab stack may function as an electrical interconnect between the plates of the anode. Similarly, the tabs of the cathode plates may be aligned with each other in a stack and electrically connected to each other to collectively form a cathode of the battery. In some examples, such a battery may be referred to as a flat or stacked plate battery.

In some examples, each electrode plate includes a current collector and anode or cathode active material on the current collector. The current collector may include a conductive layer having opposing major surfaces forming a main body, with the tab extending or projecting from the main body. The main body and tab may be integral, e.g., formed from a single piece of material, or they may be separate pieces of the same or different material, which are mechanically, electrically, and/or chemically attached. The active material also may be employed in the form of a layer, e.g., on one or more of the major surfaces of the current collector. For example, each electrode plate may comprise one or more layers of the active material, with each layer being adjacent (e.g., directly on) a major surface of the current collector.

In some examples, the electrode plates are electrically insulated from each other by separators disposed between the plates. The separators may take various forms but are typically porous nonconductive materials formed as a bag or pouch. Porous nonconductive materials which may be used include porous polyethylene or porous polypropylene. Each bag may substantially or completely surround the main body of the current collector and the active material, and the bag is sealed to the main body of the current collector across one or both sides of a base of the tab, such that at least some portion of the tab is exposed. The sealed electrode plates are stacked in an alternating configuration (e.g., alternating between anode plates and cathode plates) to form at least a portion of a battery assembly.

IMDs used to provide cardiac rhythm management therapy may require high power batteries having a capacity of at least about 5 Ah. Primary lithium batteries may be used in such applications, given the high volumetric energy density of metallic lithium used as the anode active material. During a typical charge step of cell cycling in lithium metal batteries, lithium cations can gain electrons to form lithium metal. This reduction of lithium cations can occur on a surface or edge of the lithium metal of the anode active material, resulting in growth or plating of lithium metal from the surface or edge. The operation of a lithium metal primary batteries and/or lithium ion secondary batteries, e.g., in the form of a stacked assembly as described above, may be undesirably affected if growth of lithium metal occurs from a lithium metal anode, through the separator, to the exposed portion of a cathode tab.

The rate and extent to which lithium plating occurs may depend on any number of intrinsic and/or environmental factors such as temperature within and immediately surrounding the cell. A lithium metal battery employed in an IMD may be subjected to thermal gradients across the battery depending on where and how the IMD is implanted. For example, if an IMD is implanted in a pectoral muscle, the battery may be subjected to thermal gradients caused by body temperature increasing inwards towards the body core, away from the skin. In such examples, for a stacked plate battery assembly, the side of the stack nearest the skin may be a lower temperature than the opposing side of the battery stack that is furthest from the skin, e.g., based on the influence of a patient's body temperature. Induced temperature gradients may occur continuously as heat flows through the IMD, resulting in voltage differences across the metallic lithium anode.

Temperature difference may affect lithium plating such that lithium ions may discharge on the colder side and plate on the hotter side. Orientation of the hot and cold sides of the anode may depend upon how the IMD is oriented in a patient's body, and at least in some cases, orientation of the implanted IMD may change over time thus changing the direction of any existing thermal gradient and lithium plating.

In accordance with some examples of the disclosure, a battery assembly is described, and in at least some examples, the assembly includes a plurality of anode plates and a plurality of cathode plates alternately arranged to form an electrode stack. Each plate includes a current collector and active material. The anode plates and the cathode plates are electrically insulated from each other using separators interspersed between the plates. Electrical connections between cathode plates are made by contact between exposed cathode tabs projecting from the plates; the cathode tabs are exposed in the sense that they are not insulated by the separators. Likewise, electrical connections between anode plates are made by contact between exposed anode tabs projecting from the plates.

The battery assembly, in at least some examples, includes lithium metal as the anode active material. For some or all of the anode plates, lithium metal is recessed relative to its nearest exposed cathode tab, meaning, e.g., that a section or portion of an outer edge of the lithium metal of an anode plate forms a recess relative to the nearest exposed portion of a cathode tab. Recessing the lithium anode material on the anode plate relative to an exposed portion of an adjacent cathode plate may be referred to as "scalloping" of the anode or anode material.

The arrangement of recessed anode plates may vary. In some examples, an outermost anode plate of an electrode stack includes recessed lithium metal, and in other examples, both outermost anode plates include recessed lithium metal. Such a configuration may be useful where one or more outer surfaces of the battery assembly are subjected to, or are likely to be subjected to, higher temperatures as compared to the inner areas of the assembly. If more than one anode plate includes recessed lithium metal, the amount of recess may be the same or different.

In some examples, the outermost anode plate of an electrode stack includes a certain amount of recessed area, and any one or more of the inner and outer anode plates include the same amount or a different amount of recessed area. The relationship between the plates, in terms of the amount of recessed area per plate, may be such that a gradient exists, for example, the recessed area may be largest for an outermost anode plate, and the amount may decrease for each successive anode plate. Such a configuration may be useful for a battery assembly likely to be subjected to higher temperatures on a given side, compared to other sides. The relationship between the plates, for another example, in terms of the amount of recessed area per plate, may be such that the amount may decrease for each of the successive anode plates toward the center of the electrode stack, and then the amount may increase thereafter. Such a configuration may be useful for a battery assembly likely to be subjected to higher temperatures on more than one side.

For a given anode plate and an adjacent cathode plate, scalloping or recessing the anode active material increases the shortest distance between an outer edge of the anode active material and the exposed portion of the cathode tab projecting from the adjacent cathode plate, e.g., as compared to a configuration in which the anode active material is directly adjacent to the exposed portion of the cathode tab. By recessing the anode active material in such a manner, the distance that the lithium (or anode active material) needs to plate in order for the battery to short is increased, which may increase the life of the battery assembly.

Additionally, or alternatively, recessing the anode active material may underbalance the cathode locally, which may put more burden on this edge of the lithium (or anode active material) to support its adjacent cathode as well as that cathode material that does not have lithium to balance it. As a result, the lithium edge (or anode active material edge) may discharge more quickly than a typical edge (or edge without recession or scalloping). At some larger amount of scalloping/recessing, the rate of reduction from discharge may exceed the rate of plating and the net growth of the edge may be zero or always reducing. Put another way, the rate of lithium discharge may depend on the amount of area ratios between the anode and cathode. In some examples, battery assemblies may be nominally designed with equal areas to gain the full benefit of battery power. In cases in which there is more anode area than cathode area, the unopposed anode area won't discharge substantially. Conversely, if there is less area of the anode compared to the cathode, then the anode that is close to the unopposed cathode will discharge at a higher rate in order to support the cathode lacking the locally-opposing cathode. The result is that the edge of the lithium recedes. The larger the recession of the anode active material, the higher the local edge erosion. The plating mechanism grows the edge of the lithium (or anode active material). If the edge grows to the edge of the separator bag of the anode, it can put pressure on the separator bag. Likewise, the lithium may grow through opening in the separator bag (normal openings or defects). As such, in some examples, the balance between edge erosion and edge growth of the anode active material may be balanced/adjusted by the size/distance of the recessed active anode material.

In addition to, or as an alternative to, the plating of lithium on an anode active material, in some examples, the active material of a cathode plate in a battery assembly may expand during the operating life of a battery (e.g., during discharge of the battery). In some examples, the expansion of the cathode active material may cause the cathode active material and/or separator enclosing the cathode active material to interact (e.g., come into contact) with an adjacent anode current collector (e.g., anode tab). In some examples, as a result of the cathode active material expansion, the edge of an anode tab may contact the separator surround the cathode active material such that the edge of the anode tab damages (e.g., punctures) the separator. Additionally, or alternatively, the expansion of the cathode active material may cause the cathode active material to contact an exposed portion of the anode tab, which may be undesirable to the operation of the battery.

In accordance with some examples of the disclosure, a battery assembly may include an anode plate including an anode current collector having a tab portion, and a cathode plate adjacent the anode plate, wherein a second active material on a cathode current collector of the cathode plate is recessed relative to the tab portion of the anode current collector. As will be described below, recessing the second active material of the cathode plate may increase the nearest distance between the tab portion of the anode current collector to prevent the second active material and/or a separator over the second active material from contacting, e.g., an edge of the tab portion of the anode current collector when the second active material expands during the operating life of the battery assembly. In some examples in which the battery assembly include a plurality of cathode plates, the active material of each cathode plate may be recessed relative a tab portion of an adjacent anode current collector, e.g., rather than only some of the cathode plates having recessed active materials.

In some examples, a battery assembly may include anode plates having recessed active material in the manner described herein as well as cathode plates having recessed active material in the manner described herein. In other examples, only anode plate(s) of a battery assembly may have recessed active material in the manner described herein or only cathode plate(s) of a battery assembly may have recessed active material in the manner described herein.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has battery 26 positioned within an outer housing 40 of the IMD 16. Battery 26 may be a primary or secondary battery (e.g., a lithium primary battery or a lithium ion secondary battery).

While the examples in the disclosure are primarily described with regard to battery 26 positioned within housing 40 of IMD 16 for delivery of electrical therapy to heart of patient 12, in other examples, battery 26 may be utilized with other implantable medical devices. For example, battery 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), or the like. Moreover, while examples of the disclosure are primarily described with regard to implantable medical devices, examples are not limited as such. Rather, some examples of the batteries described herein may be employed in any medical device including non-implantable medical devices. For example, an example battery may be employed to supply power to a medical device configured delivery therapy to a patient externally or via a transcutaneously implanted lead or drug delivery catheter.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition (s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMD 16 in order to monitor electrical activity of heart 14. In one example, the sensing circuitry may include switching circuitry to select which of the available electrodes on leads 18, 20, and 22 of IMD 16 are used to sense the heart activity. Additionally, the sensing circuitry of IMD 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as battery 26, which may be a lithium primary battery. Battery 26 may be capable of holding a charge for several years. In general, battery 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, and/or delivery of a therapeutic drug fluid. Battery 26 may include a lithium-containing anode and cathode including an active material that electrochemically reacts with the lithium within an electrolyte to generate power.

Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels) until a fibrillation of heart 14 is stopped. IMD 16 may detect fibrillation by employing one or more fibrillation detection techniques known in the art. For example, IMD 16 may identify cardiac parameters of the cardiac signal (e.g., R-waves), and detect fibrillation based on the identified cardiac parameters.

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 42. For example, leads 18, 20, and 22 are connected to IMD 16 using the lead connector ports in connector block 42. Once connected, leads 18, 20, and 22 are in electrical contact with the internal circuitry of IMD 16. Battery 26 may be positioned within the housing 40 of IMD 16. Housing 40 may be hermetically sealed and biologically inert. In some examples, housing 40 may be formed from a conductive material. For example, housing 40 may be formed from a material including, but not limited to, titanium, stainless steel, among others.

Figure 2:
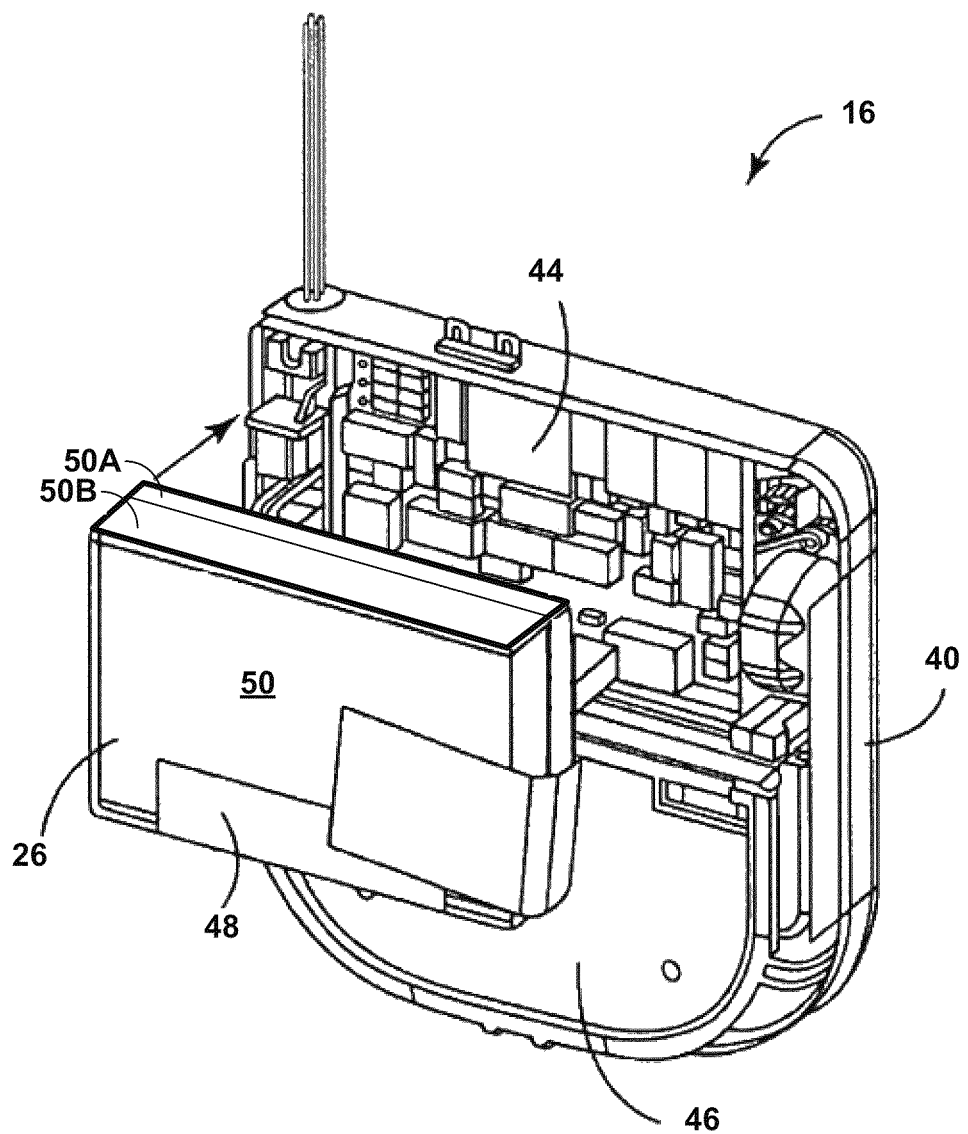
FIG. 2 is a conceptual diagram illustrating a partial exploded view of the IMD of FIG. 1.

FIG. 2 is a conceptual diagram of IMD 16 of FIG. 1 with connector block 42 not shown and a portion of housing 40 removed to illustrate some of the internal components within housing 40. IMD 10 includes housing 40, a control circuitry 44 (which may include processing circuitry), battery 26 (e.g., an organic electrolyte battery) and capacitor(s) 46. Control circuitry 44 may be configured to control one or more sensing and/or therapy delivery processes from IMD 16 via leads 18, 20, and 22 (not shown in FIG. 2). Battery 26 includes battery assembly housing 50 and insulator 48 (or liner) disposed therearound. Battery 26 charges capacitor(s) 46 and powers control circuitry 44.

Figure 3:
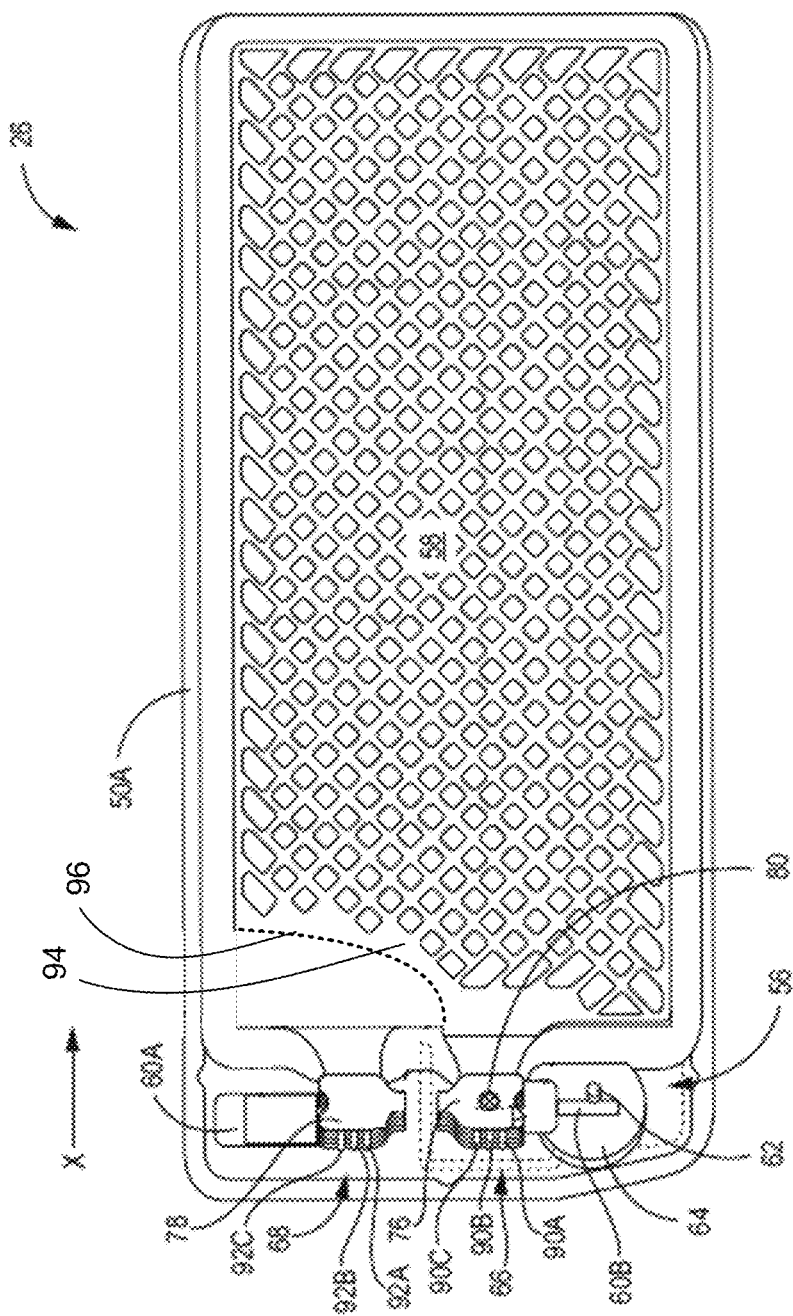
FIG. 3 is a conceptual diagram illustrating a plan view of an example battery assembly in accordance with examples of the disclosure.

FIG. 3 is a conceptual diagram illustrating aspects of example battery 26. Battery 26 includes assembly housing 50 having a bottom housing portion 50A and top housing portion 50B (shown in FIG. 2), a feed-through assembly 56, and an electrode assembly 58. An electrolyte may be filled into the enclosure via a fill port (not shown) in housing 50. Housing 50 houses electrode assembly 58 with the electrolyte. Top portion 50B and bottom portion 50A of housing may be welded or otherwise attached to seal the enclosed components of battery 26 within housing 50. Feed-through assembly 56, formed by pin 62 and insulator member/ferrule 64, is electrically connected to jumper pin 60B. The connection between pin 62 and jumper pin 60B to form the positive terminal of the battery. Conductor 60A is electrically connected to the housing 50A to form the negative terminal of the battery.

As noted above, a fill port (not shown) allows for the introduction of liquid electrolyte to electrode assembly 58. The electrolyte creates an ionic path between anode 66 and cathode 68 of electrode assembly 58. The electrolyte serves as a medium for migration of ions between anode 66 and cathode 68 during an electrochemical reaction with these electrodes.

Electrode assembly 58 is depicted as a stacked assembly (also referred to as a stacked plate assembly). Cathode 68 comprises a set of sealed cathode plates with set of tabs 78 projecting from respective cathode plates disposed within separator bags (described below). Tabs 78 may be electrically coupled to each other and to conductive member 60A. Side welds 92A-92C may be employed to mechanically couple tabs 78 to each other, provide stability to the stack and/or relieve stress acquired by any one or more of tabs 78. In some examples, spacers (e.g., electrically conductive spacers may be located between respective tabs 78.

Anode 66 may be constructed in a similar manner as cathode 68. Anode 66 comprises a set of sealed anode plates with set of tabs 76 projecting from respective anode plates disposed within the separator bags (described below). Tabs 76 are arranged in a stacked configuration. Optional alignment member 80 extends through tabs 76 vertically, from the top tab to the bottom tab through an aperture formed in each tab. Although not shown in FIG. 3, cathode tabs 78 may have a similar optional alignment member extending therethrough. Side welds 90A-90C may be employed to mechanically couple tabs 78 to each other, provide stability to the stack and/or relieve stress acquired by any one or more of tabs 76. In some examples, spacers (e.g., electrically conductive spacers may be located between respective tabs 76.

As will be described further below, one or more anode plates of electrode assembly 58 may have a recessed perimeter portion. For example, as show in FIG. 3, first anode current collector 94 includes a recessed portion defined by first nearest perimeter 96. The recessed portion is recessed relative to an exposed portion of cathode tabs 78.

Materials used to form the anode and cathode current collectors may be any useful conductive material such as titanium, aluminum, nickel (e.g., for the anode current collector), copper and/or alloys thereof. First active material comprises the active material of the anode and may be referred to herein as the anode active material. The first active material may comprise any useful anode material capable of releasing an electron under conditions in which the battery assembly is being used. The first active material may comprise an active metal such as lithium metal. The active material used for the cathode (referred to herein in some instances in the cathode active material) may comprise any useful material capable of being reduced under conditions in which the battery assembly is being used. For example, the cathode active material may comprise a metal oxide such as lithium cobalt oxide, $Li_{1-x}CoO_2$. Other examples of the cathode active material include metal oxides such as vanadium oxide, silver vanadium oxide (SVO), manganese dioxide, etc., carbon monofluoride $CF_x$ and hybrids of carbon monofluoride such as $CF_x+MnO_2$, or a combination silver vanadium oxide (CSVO).

Figure 4A:
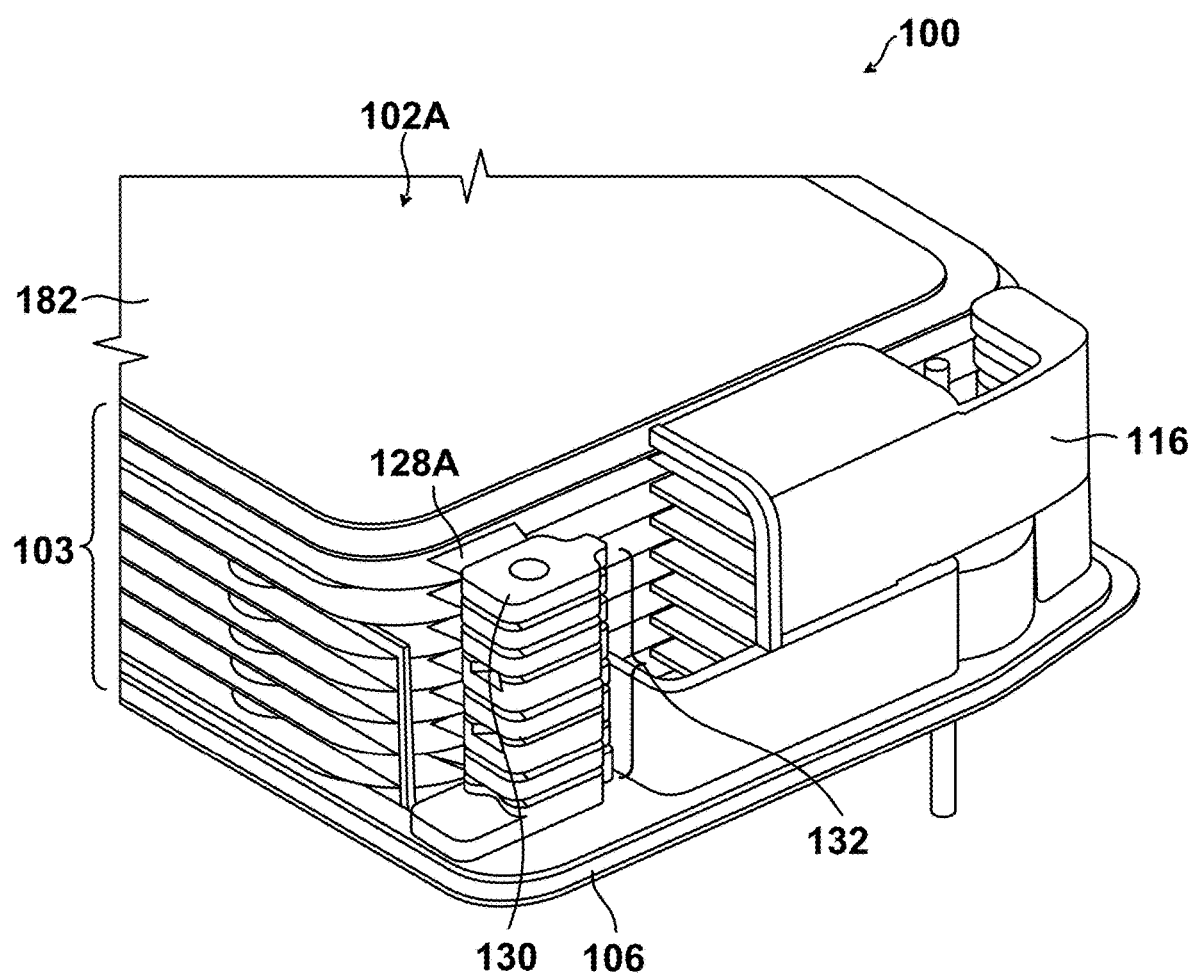
FIGS. 4A-4D are conceptual diagrams illustrating a perspective view of portions of an example battery assembly in accordance with examples of the disclosure.

FIGS. 4A-4D are conceptual diagrams illustrating a perspective view of portions of example battery assembly 100. Battery assembly 100 may be the same or substantially similar to all or a portion of battery 26 shown in FIG. 3. Example battery assembly 100 comprises stack 104 alternating between sealed anode plates 102 and sealed cathode plates 104 arranged as a stack on cover 106. Only the topmost sealed anode plate 102A is visible in the perspective view shown in FIG. 4A. FIGS. 5A-5C are conceptual diagrams illustrating a different perspective view of portions of the same battery assembly 100 shown in FIGS. 4A-4C. In FIGS. 5A-5C, battery assembly 100 is shown from a bottom view, without cover 106, such that bottommost sealed anode plate 102H is viewable in FIG. 5A.

Each sealed anode plate of set 102 includes anode plate 180, and each anode plate includes anode current collector 112 and first (anode) active material 114 on one or both opposing major surfaces of anode current collector 112. First active material 114 is present on a major surface of an anode current collector, e.g., when that major surface is adjacent a cathode plate. For battery assembly 100, each of the outermost (e.g., "top" and "bottom") sealed anode plates 102A and 102H in the stack of electrode plates may have one layer of first active material 114A and 114H on an inner facing major surface of the respective current collectors 112A and 112H. For battery assembly 100, additional sealed anodes plates (not shown) are present in between outermost sealed anode plates 102A and 102H. Each of these additional sealed anode plates includes two layers of the first active material, one on each opposing major surface of the current collector. FIG. 4D shows battery assembly 100 in which topmost sealed cathode plate 104A is removed from view. First active material 114B of the sealed anode plate below sealed anode plate 102A comprises two layers, with anode current collector 112B (not shown) between the two layers. In the example of FIG. 4D, first active material 114A of the top most sealed anode plate 102A includes a recessed portion, and first active material 114B of the sealed anode plate below the top most sealed anode plate 102A does not include a recessed portion as shown in FIG. 4D.

The battery assembly described in this disclosure may have any number of sealed anode plates between outermost sealed anode plates 102A and 102H. In some examples, there may be six additional sealed anode plates between sealed anode plates 102A and 102H, for a total of eight sealed anode plates; a total of seven sealed cathode plates may be included.

Figure 4B:
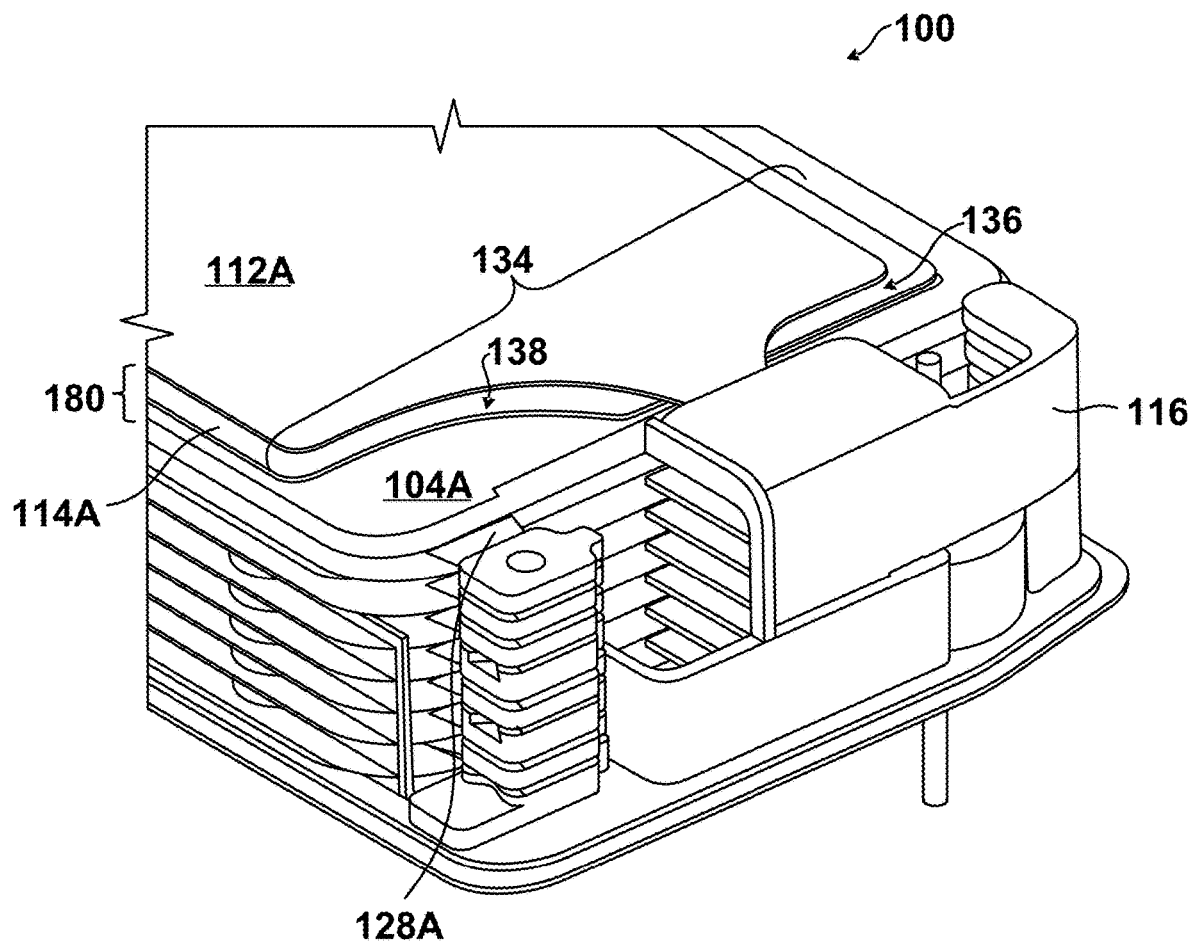
Figure 5A:
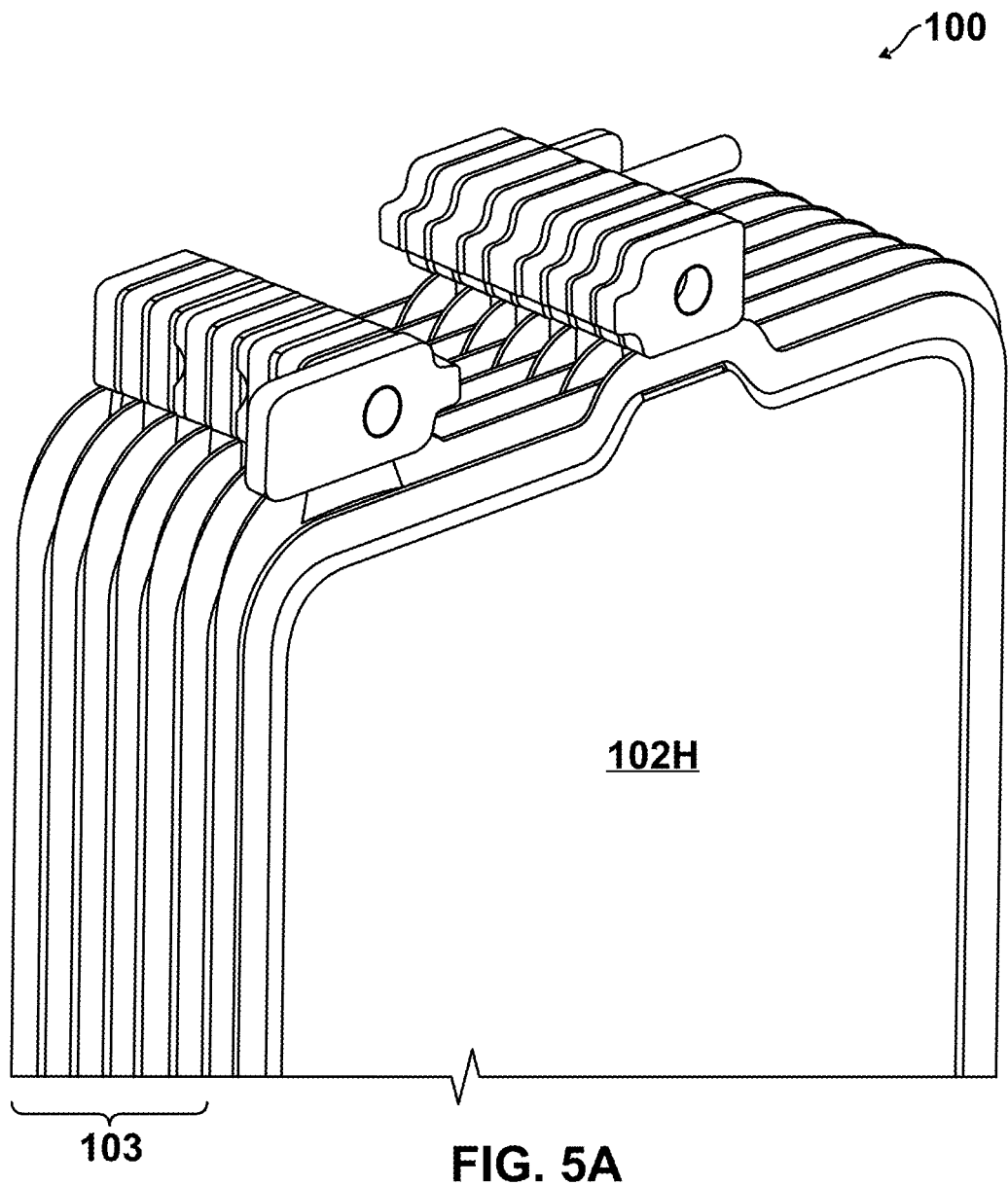
FIGS. 5A-5C are conceptual diagrams illustrating a perspective view of portions of the example battery assembly shown in FIGS. 4A-4D.
Figure 5B:
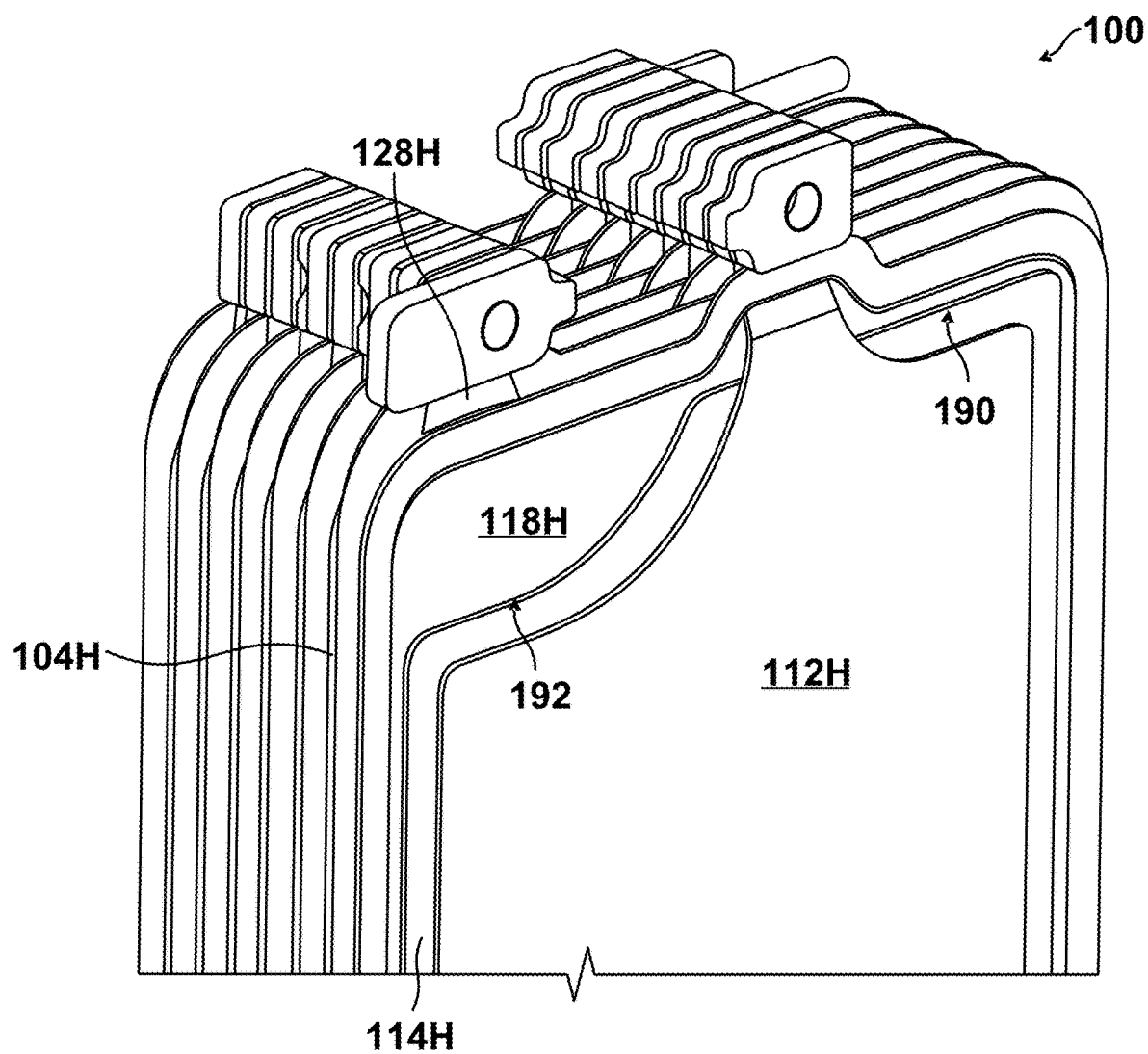
Figure 5C:
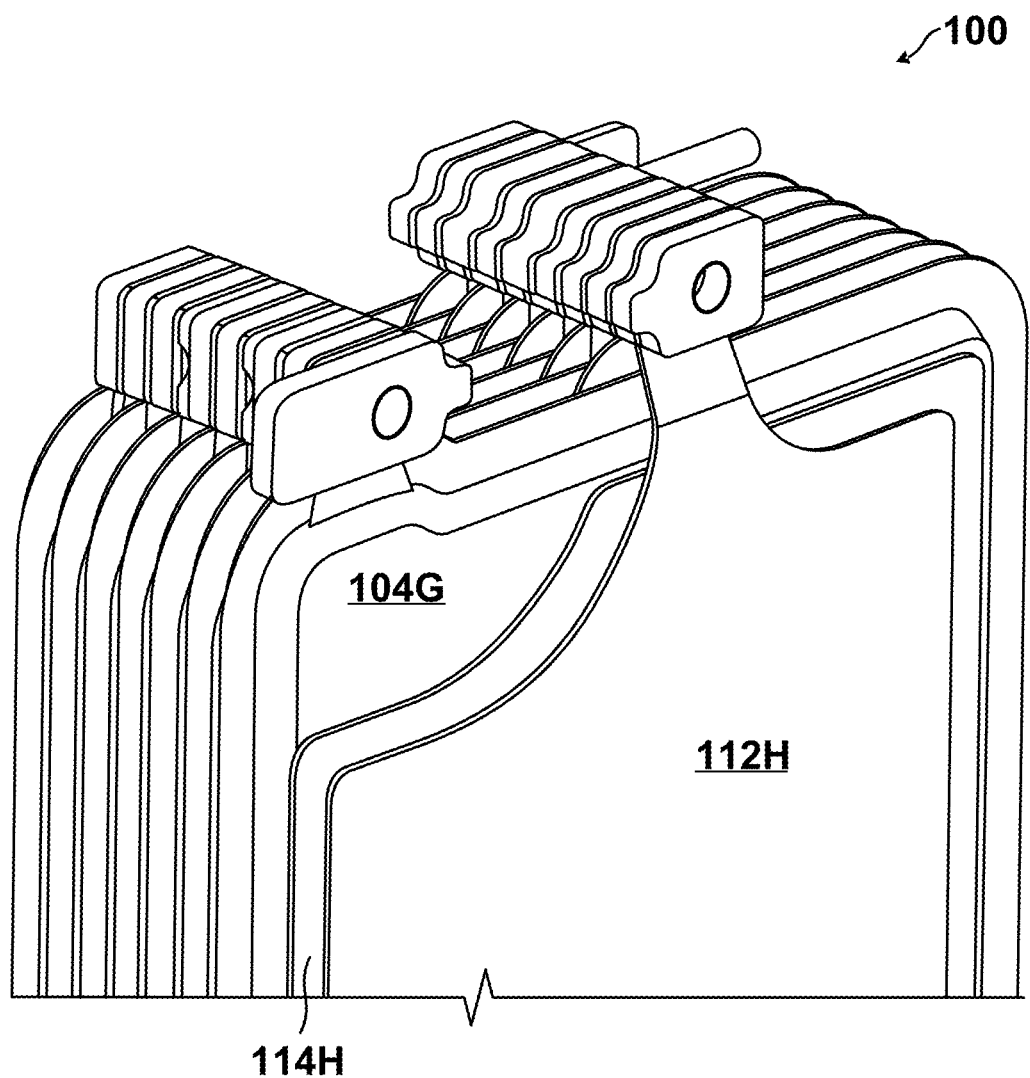

FIG. 4B shows sealed anode plate 102A without its separator bag 182 such that anode current collector 112A and underlying first active material 114A are visible. FIG. 5B shows sealed anode plate 102H without the top portion of its separator bag such that anode current collector 112H and underlying first active material 114H are visible. Bottom portion 118H of the separator bag is visible in FIG. 5B, underneath anode current collector 112H and first active material 114H. First active material 114A includes a side nearest exposed portion 128H of the adjacent cathode current collector of sealed cathode plate 104H, and this side is defined by an outer edge or perimeter that includes a substantially linear perimeter portion 190 and a recessed perimeter portion 192. First active material 114H is recessed relative to a first active material not having a recess, e.g., a first active material wherein the side nearest exposed portion 128H is substantially linear. Recessed perimeter portion 192 comprises a nearest perimeter to exposed portion 128H because it defines a portion of the perimeter of the first active material 114H that is nearest exposed portion 128H.

Figure 4C:
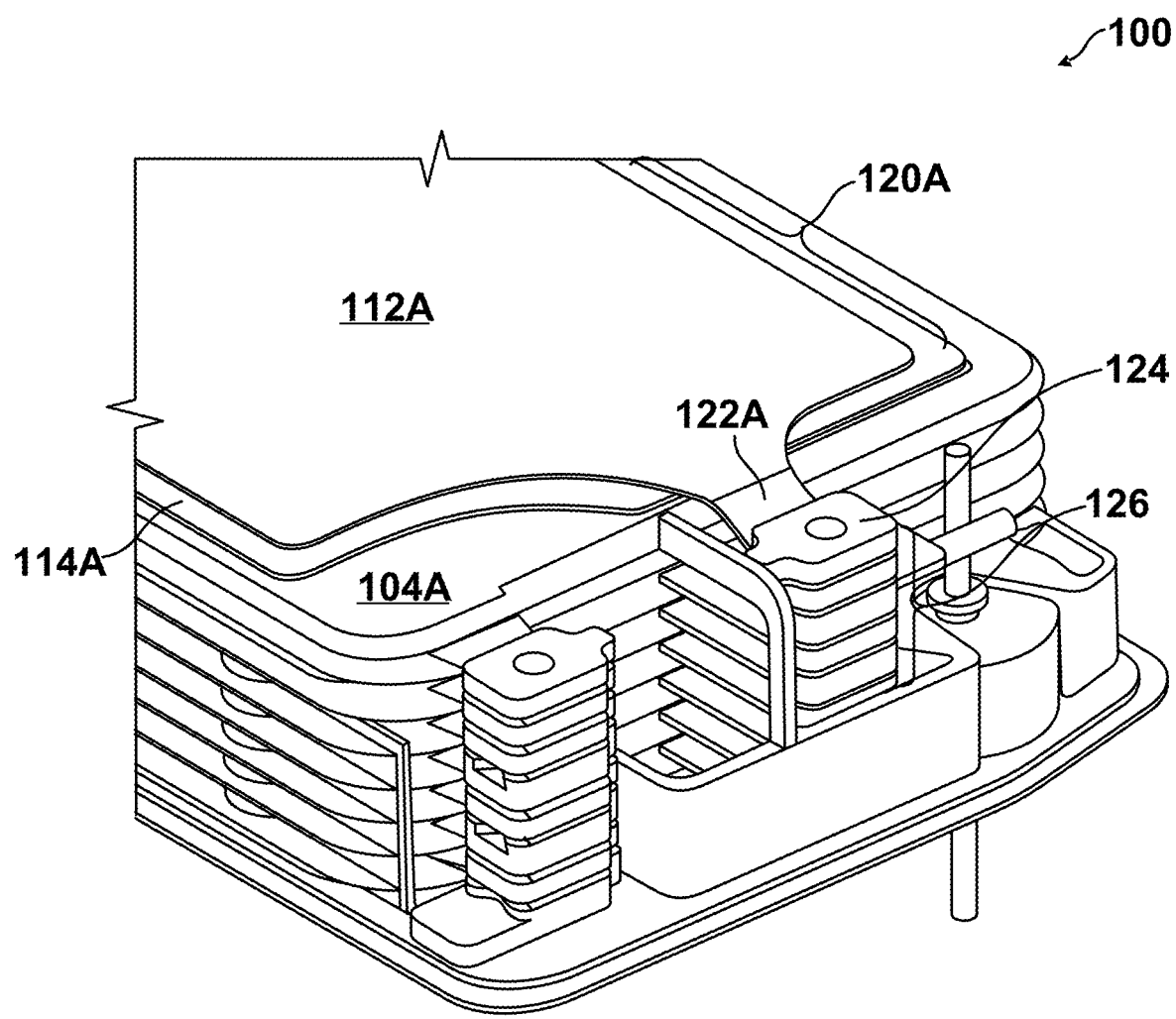
Figure 4D:
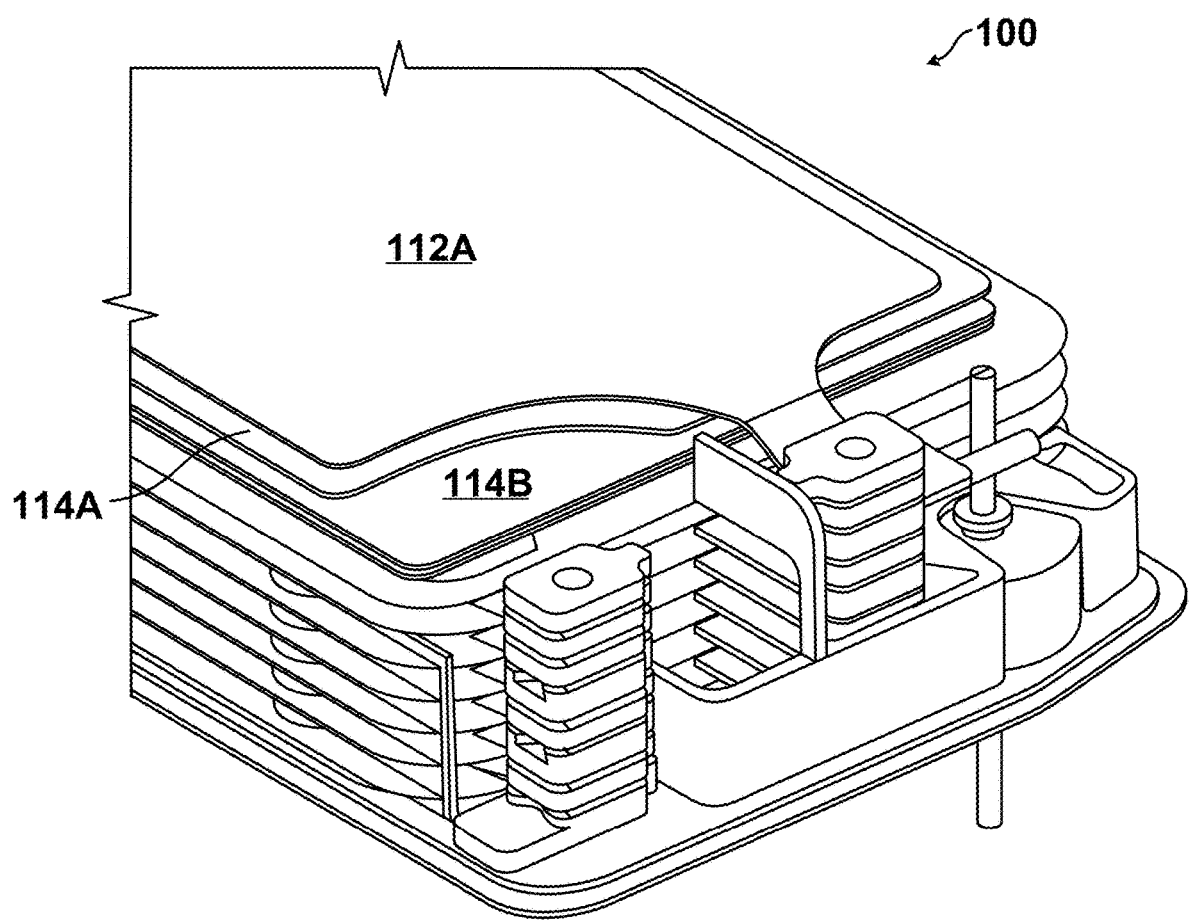

For example, battery assembly 100, each anode current collector includes a main body, formed by the two opposing major surfaces, and a tab projecting from the main body. The sealed anode plates are stacked such that the tabs are aligned, with spacers in between the tabs. FIG. 4C shows main body 120A of anode current collector 112A, and tab 122A projects from the main body. Spacer 124 is visible on top of stack 126 (partially visible) formed by additional alternating tabs and spacers. Tabs 122 and alternating spacers are located underneath headspace insulator 116 shown in FIGS. 4A and 4B.

Battery assembly 100 includes stack 103 of sealed cathode plates 104 alternately arranged with sealed anode plates 102. In FIGS. 4B and 4C, topmost sealed cathode plate 104A is visible underneath anode current collector 112A and first active material 114A. In FIG. 5C, bottommost sealed cathode plate 104G is visible behind anode current collector 112H and first active material 114H.

Each sealed cathode plate 104 includes a cathode current collector (not shown) and a second active material (not shown) on both opposing major surfaces of each cathode current collector. The second active material may also be referred to herein as the cathode active material. The cathode current collector and second active material are sealed inside a separator bag which is typically porous polymeric material formed as a bag or pouch. Each bag may substantially or completely surround the main body of the cathode current collector and the cathode active material, and the separator bag is sealed to the main body of the cathode current collector across one or both sides of a base of the tab, such that at least some portion of the tab is exposed.

The battery assembly described in this disclosure may have any number of sealed cathode plates 104 alternating with sealed anode plates 102 and between outermost sealed anodes plates 102A and 102H.

For example, battery assembly 100, each cathode current collector includes a main body, formed by the two opposing major surfaces, and tab 128 projecting from the main body. The sealed cathode plates 104 are stacked such that tabs 128 are aligned, with spacers in between the tabs. FIG. 4A shows tab 128A of topmost sealed cathode current collector 104A. Tab 128A may comprise an exposed portion because it is not sealed inside the separator bag of sealed cathode plate 104A. Spacer 130 is visible on top of stack 132 formed by additional alternating tabs 128 and spacers. Tabs 128 are not completely visible in any of FIGS. 4A-4D and FIGS. 5A-5C as they are obscured by the alternating spacers in stack 132. Each tab 128 comprises an exposed portion, and the exposed portion comprises a base of the tab.

For example, battery assembly 100, as shown in FIG. 4B, first active material 114A includes side 134 nearest exposed portion 128A of the adjacent cathode current collector of sealed cathode plate 104A. Side 134 is defined by an outer edge or perimeter that includes a substantially linear perimeter portion 136 and a recessed perimeter portion 138. First active material 114A is recessed relative to a first active material not having a recess, e.g., a first active material wherein the side nearest exposed portion 128A is substantially linear. Recessed perimeter portion 138 comprises a nearest perimeter to exposed portion 128A because it defines a portion of the perimeter of the first active material 114A that is nearest exposed portion 128A.

Figure 6:
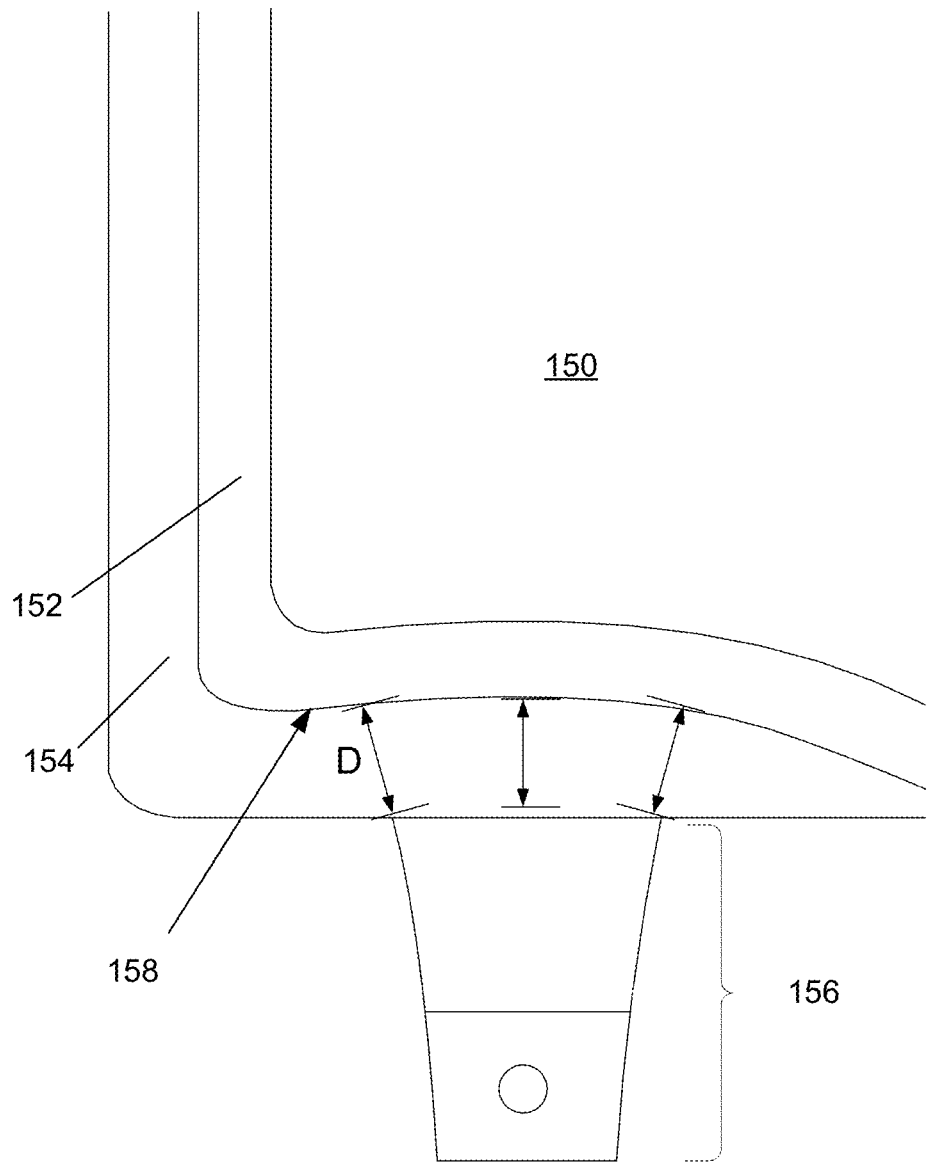
FIG. 6 is a conceptual drawing illustrating a plan view of a portion of an example battery assembly in accordance with examples of the disclosure.

FIG. 6 is a conceptual drawing illustrating a plan view of a portion of an example battery assembly, such as battery assembly 100 shown in FIGS. 4A-4D and FIGS. 5A-5C. In FIG. 6, first active material 152 is between anode current collector 150 and a sealed cathode plate wherein separator bag 154 of the sealed cathode plate is visible. In this example, first active material 152 has first recessed portion that defines a first nearest edge or first nearest perimeter 158. Exposed portion 156 of the cathode current collector (not shown) within separator bag 154 projects from separator bag 154 and is in the form of a tab. In this example, first nearest distance D defines the distance between first nearest perimeter 158 and any portion of exposed portion 156, such that D defines the minimum distance between any point on first nearest perimeter 158 and any point on exposed portion 156. In this example, first nearest perimeter 158 and exposed portion 156 are equidistant to each other, and D is substantially the same.

First active material 152 may include lithium metal, and as described above, lithium plating may occur at any edge of the lithium metal material. The recessed portion having first nearest perimeter 158 comprises a recess (also referred to as a "scallop" in some examples). Minimum distance D is greater than any minimum distance between an unrecessed first active material (e.g., of one or more other anode plates within the battery assembly) and exposed portion 156. Because of the recess, there is an increase in the distance that metal plating needs to travel during growth, before reaching exposed portion 156.

The portion of the battery assembly shown in FIG. 6 may be employed in a battery assembly such that an outermost anode plate includes the recess of the lithium metal material. If the battery assembly is used in a device which is subjected to differences in temperatures on different sides of the device, in addition to temperature gradients as described above for IMDs, the recess of an outermost plate may cause delay in time for the plated active material to lose electrical isolation with the exposed cathode tab because plating needs to occur over a longer distance as compared to a distance if the recess was not present.

The first active material of battery assembly described in this disclosure may be recessed such that a minimum distance or first distance between the first nearest perimeter and the exposed portion is any useful distance. The first distance may depend upon a number of factors such as the device in which the battery assembly is used. Design considerations of the recessed portion, including its shape and dimensions, may take into account that a decrease in battery capacity may occur as a result of the recessed portion. In some examples, the first distance between the first nearest perimeter and the exposed portion is at least about 0.6 mm. In some examples, the first distance between the first nearest perimeter and the exposed portion is from about 0.6 mm to about 2.5 mm. In some examples, the first distance between the first nearest perimeter and the exposed portion is from about 1.0 mm to about 2.0 mm.

Figure 7A:
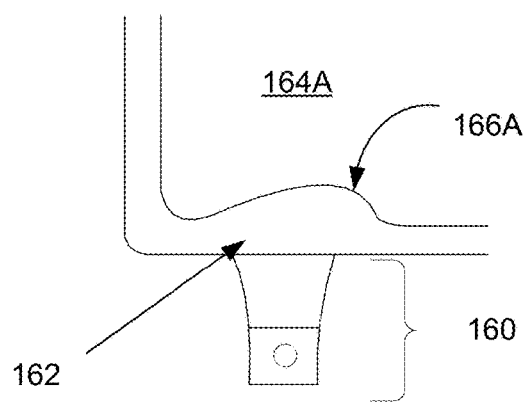
FIGS. 7A-7D are conceptual drawings illustrating plan views of a portion of an example battery assembly in accordance with examples of the disclosure.
Figure 7B:
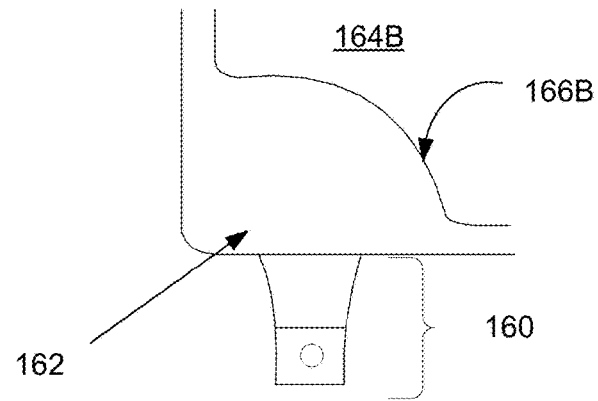
Figure 7C:
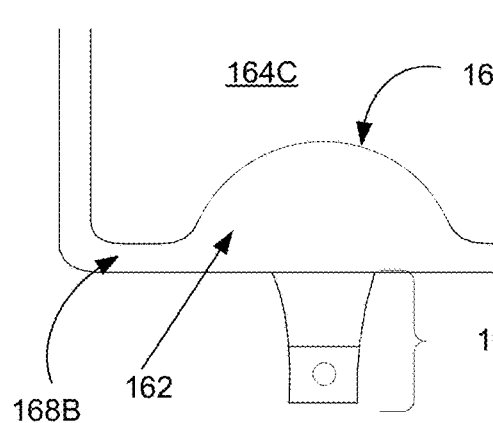
Figure 7D:
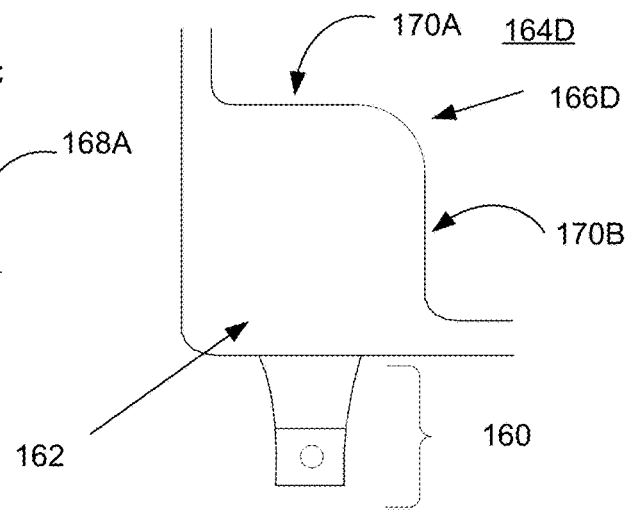

FIGS. 7A-7D are conceptual drawings illustrating plan views of a portion of an example battery assembly, in which the recessed portion of the first active material comprises different shapes. Exposed portion 160 projects from separator bag 162 of a cathode plate. In FIG. 7A, first active material 164A has nearest perimeter 166A that is asymmetrically curved. In FIG. 7B, first active material 164B has nearest perimeter 166B that is symmetrically curved. In FIG. 7C, first active material 164C has nearest perimeter 166C that is shaped as a semicircle such that substantially linear edge or perimeter 168 of first active material 164C comprises two portions 168A and 168B. In FIG. 7D, first active material 164D has nearest perimeter 166D comprising edges 170A and 170B that are substantially perpendicular to each other. Any suitable shape for the recessed perimeter is contemplated.

Figure 8A:
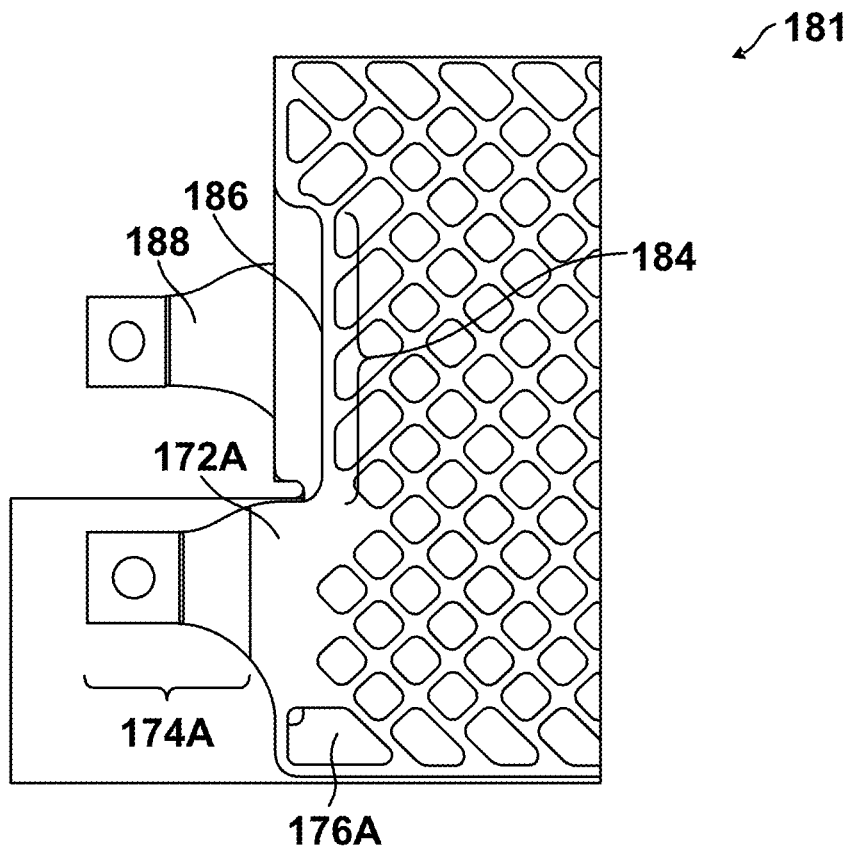
FIGS. 8A and 8B are conceptual drawings illustrating plan views of a portion of an example battery assembly in accordance with examples of the disclosure.
Figure 8B:
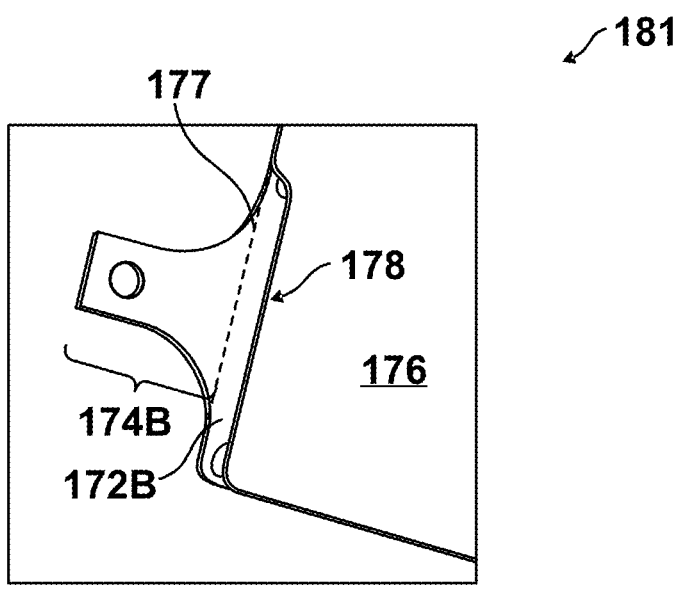

FIGS. 8A and 8B are conceptual drawings illustrating plan views of a portion of an example battery assembly 181 which may be substantially similar to that of such as battery 26 and/or battery assembly 100 including one or more anode plate and one or more cathode plates in a stacked configuration. In the portion illustrated in FIG. 8A, cathode current collector 172A (shown without the cathode active material for ease of illustration) of a cathode plate is overlying an anode plate having anode tab 188 and anode active material 176 on an anode current collector (not shown). Cathode current collector 172 comprises cathode tab 174 that is exposed (e.g., not covered with active cathode material) when the cathode current collector, comprising cathode active material on opposing major surfaces of cathode current collector 172, is sealed with a separator bag as described, e.g., with regard to battery assembly 100. In this example, first active anode material 176 may comprise lithium metal, and the first active material is recessed as shown by nearest perimeter 178 in the manner described above for battery assembly 100.

FIG. 8B shows cathode current collector 172B of the cathode plate underlying first active anode material 176 of the anode plate shown in FIG. 8A. As shown, first active material 176 is recessed relative to exposed cathode tab 174B of the underlying cathode plate, e.g., rather than the perimeter of the active anode material being along dashed line 177, in the same manner as described above for battery assembly 100.

As described herein, in some examples, in addition to or as an alternative to the recessing/scalloping of anode active material relative to exposed cathode tabs, one or more cathode plates of a battery assembly may have similar recessing/scalloping of the cathode active material relative to anode tabs of adjacent (underlying and/or overlying) anode plates. In some examples, the scalloping/recessing of the active material of the cathode may be present to reduce potential pressure from an adjacent anode tab on the cathode which may occur as the cathode active material swells (e.g., during the operating life of the battery). For example, pressure of the anode tab on the cathode separator bag may depend on the proximity of the anode tab and bending/flexing of the anode tab in the electrode stack interconnect. Unlike some examples of recessing/scalloping of anode active material which may be to address issues associated with a temperature/voltage gradient across a stack of electrode plates of a battery assembly, all or substantially all cathode plates in a stack may include scalloping/recessing of the cathode active material relative to adjacent anode tab(s) since the expansion of the cathode active material may be present in all cathode plates compared to plating of the anode active material, which may be biased to one side of the electrode stack of a battery assembly, as described herein.

FIG. 8A also shows an example of cathode scalloping/recessing. As shown, cathode current collector 172A is recessed/scalloped along perimeter 186 in area 184 of the cathode current collector 172A. The outer perimeter of cathode current collector 172A shown in FIG. 8A may generally correspond to the perimeter of the active material (not shown in FIG. 8A) of the cathode plate including the current collector 172A. In the example of FIG. 8A, the active material of the cathode plate is recessed/scalloped relative to exposed anode tab 188 of the underlying anode plate current collector by the "notched" portion of area 184 of cathode current collector 172A. Additional examples of cathode recessing/scalloping are described in further detail below with regard to FIGS. 12A-12F and 13.

Figure 9:
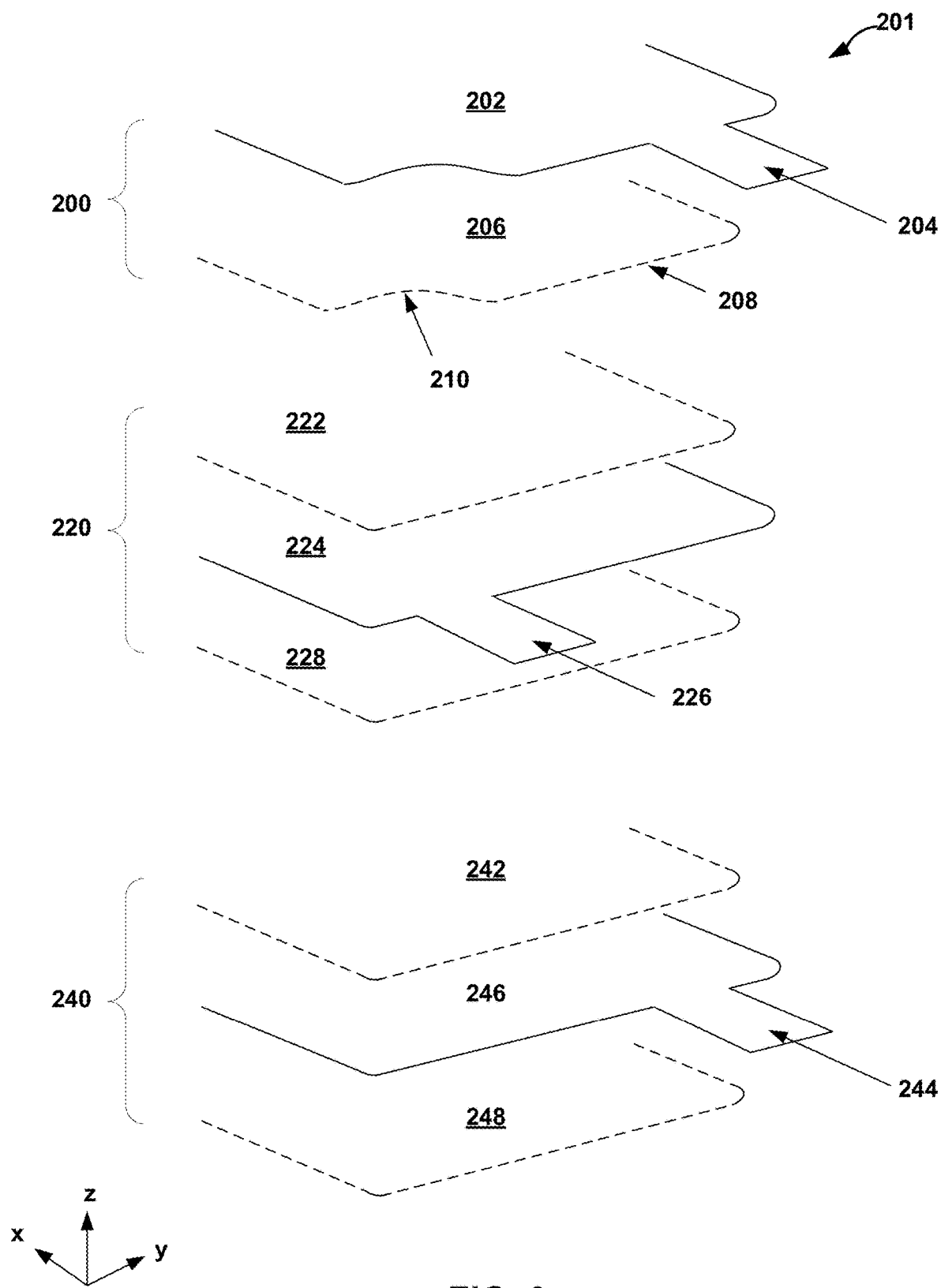
FIG. 9 is a conceptual drawing illustrating a perspective view of a portion of an example battery assembly in accordance with examples of the disclosure.

FIG. 9 is a conceptual drawing illustrating an exploded perspective view of a portion of an example battery assembly 201 in accordance with this disclosure. In this example, battery assembly 201 includes a stack comprising first anode plate 200, first cathode plate 220, and second anode plate 240. First anode plate 200 includes first anode current collector 202 having tab 204, and first active material 206 is deposited over a major surface of the current collector (the underside of the current collector). First active material 206 includes a recessed portion having first nearest perimeter edge 210. First cathode plate 220 includes cathode current collector 224 having tab 226. Cathode active material comprises two layers 222 and 228, one on each opposing major surface of cathode current collector 224. Second anode plate 240 includes second anode current collector 246 having tab 244, disposed between two layers of second active material 242 and 248, one on each opposing major surface of second anode current collector 246.

In the example shown in FIG. 9, first active material 206 and second active material 242 and 248 may comprise lithium metal. First active material 206 includes a portion recessed relative to tab 226 of cathode plate 224, and second active material 242 and 248 are not recessed relative to tab 226 of cathode plate 224. In the example of FIG. 9, the perimeter of active material 242 and 248 are the closer to the tab 226 of cathode plate 224. As described herein, in other examples, active material 242 and/or 248 may be recessed relative to tab 226, e.g., to the same degree as active material 206 or to a lesser degree. Separator bags (not shown) are used to insulate electrically the alternating electrode plates leaving the tabs exposed. For example, cathode plate 220 is sealed inside a separator bag such that cathode tab 226 is an exposed portion. By recessing first active material 206, advantages as described above may be obtained while any decrease in battery capacity is minimized because the second active material 242 and 248 are not recessed.

Figure 10A:
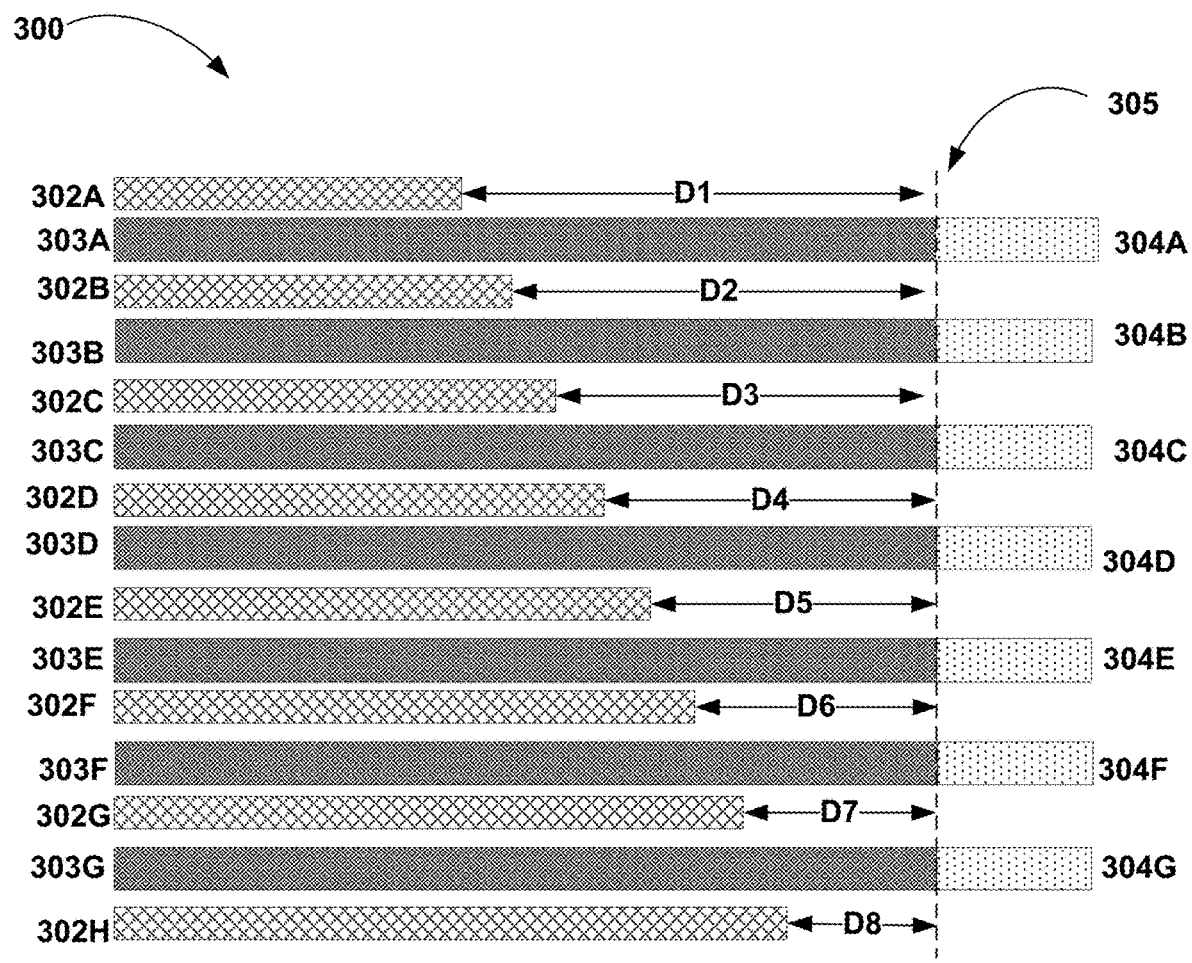
FIGS. 10A and 10B are conceptual drawings illustrating cross-sectional views of a portion of an example battery assembly in accordance with examples of the disclosure.

As described above, the battery assembly described in this disclosure may be employed in an IMD and therefore may be subjected to differences in body temperature depending on how the implant is oriented in a patient. Lithium plating may occur more quickly and to a greater extent on a side of the assembly adjacent a warmer area of a patient (e.g., the side of a battery assembly facing inward away from the skin of the patient), as compared plating occurring on a side adjacent a cooler area (e.g., the side of a battery assembly facing towards the skin of a patient). FIG. 10A is a conceptual drawing illustrating a cross-sectional view of a portion of another example battery assembly 300 that may be employed in such an 1 MB. Battery assembly 300 may be substantially similar to battery assembly 100. In this example, battery assembly 300 comprises first active anode material 302A to eighth active anode material 302H. Active materials 302A-302H may be disposed on respective anode current collectors which are not shown in FIG. 10A for ease of illustration. As described above, each anode plate that is not an outermost anode plate may comprise two layers of anode active material, one layer on each side of the respective anode current collector. Only one layer of anode active material for each of these inner anode plates is shown in FIG. 10A for ease of illustration, e.g., anode active material 302B is representative of both layers of active anode material that may be present on the second anode current collector, and so forth through 302G. The cathode active material and separator portions (e.g., separator bags) of the electrode stack of battery assembly 300 are also not shown in FIG. 10A for ease of illustration.

Battery assembly 300 also includes first cathode current collector 303A having exposed portion 304A, to seventh current collector 303G having seventh exposed portion 304G. Active anode material 302 may comprise lithium metal. First active material 302A includes a recessed portion as indicated by distance D1 between nearest perimeter of the first active material and a location on exposed tab 304A that is nearest the nearest perimeter as identified by axis 305. Distance D2 through distance D8 are also indicated and are as described for D1 with respect to pairs of active material 302 and exposed portions 304. An IMD including example battery assembly 300 may be implanted in a patient such that the IMD is oriented with a side nearest D1 adjacent to the trunk of a patient (a warmer region), and a side nearest D8 adjacent to the skin of the patient (a cooler region). Distance D1 is greater than distance D2, which is greater than distance D3, and so forth.

FIG. 10A illustrates an example stacked plate battery assembly 300 in which the recession of the active material 302 of anode plates displays a gradient along the electrode stack relative to exposed portions 304 of cathode plates 303. In other examples, the active material 302 of respective anode plates in an electrode stack may be recessed relative to exposed portions 304 only on one or both of the "top" and "bottom" anode plates of an electrode stack with the active material 302 of the intermediate anode plates not being recessed relative to exposed portions 304. In other examples, the active material 302 of one or both of the "top" and "bottom" anode plates may be recessed more than the intermediate anode plates, which each may not be recessed or may be recessed to a lesser degree/distance compared to active material of the "top" and/or "bottom" anode plates in an electrode stack. In other examples, the active material 302 of the "top" or "bottom" plate may be recessed more than the active material 302 of the remaining anode plates, where the active material 302 of the other anode plates in the electrode stack all have a nearest perimeter that is the substantially same distance from exposed portions 304.

Figure 10B:
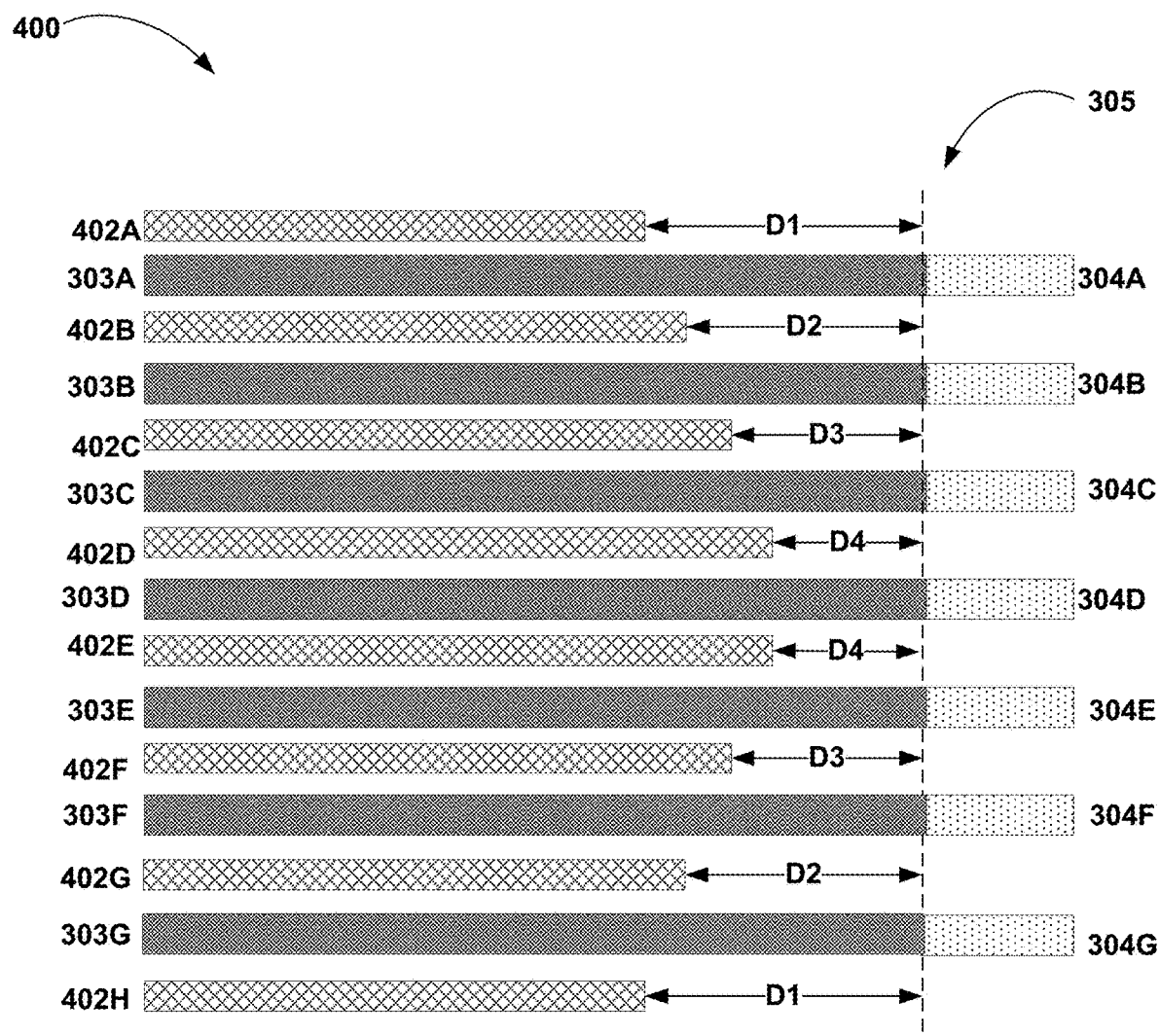

FIG. 10B is a conceptual drawing illustrating a cross-sectional view of a portion of example battery assembly 400 that may be employed in an IMD. Battery assembly 400 may be substantially similar to battery assembly 300. Battery assembly 400 also includes cathode current collectors 303 having exposed portions 304, as described above for FIG. 10A. Battery assembly 400 includes anode active material 402, which may be disposed on corresponding anode current collectors (not shown). Anode active material 402 may comprise lithium metal.

However, in the example of FIG. 10B, the recess distance D from the nearest perimeter edge of each anode active material 402 from its corresponding exposed portion 304 of cathode tab 304 decreases for active material 402A to 402D from D1 to D4 moving from the "top" of the electrode stack to the "middle" of the electrode stack, and then increase again for active material 402E-402H from the "middle" to the "bottom" of the electrode stack from D4 to D1. An IMD including example battery assembly 400 may be implanted in a patient, and regardless of orientation of the IMD, outer areas of the battery assembly which are adjacent the patent may exhibit less lithium plating even though these areas are warmer. As described above, the battery assembly described in this disclosure may be employed in an IMD and therefore may be subjected to thermal gradients across the assembly.

Figure 11:
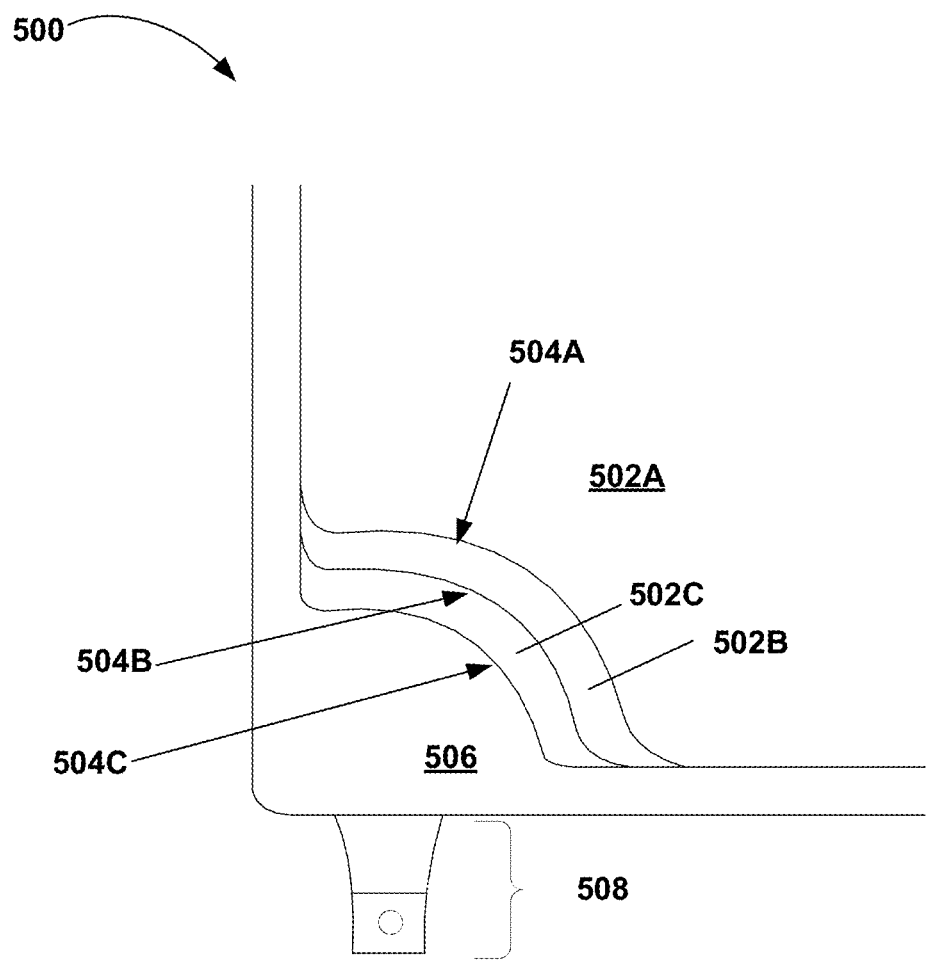
FIG. 11 is a conceptual drawing illustrating a plan view of a portion of an example battery assembly in accordance with examples of the disclosure.

FIG. 11 is a conceptual drawing illustrating a plan view of a portion of an example battery assembly 500. In this example, first active material 502A is recessed as indicated by first nearest perimeter 504A, second active material 502B is recessed as indicated by second nearest perimeter 504B, and third active material 502C is recessed as indicated by third nearest perimeter 504C. The separator bag 506 of an underlying cathode plate is visible, with exposed portion 508 projecting from out of the separator bag. In this example, the amount of recessed area associated with first active material 504A is greater than that of second active material 504B, which in turn is greater than that of third active material 504C. First nearest perimeter 504A of first active material 502A is a greater distance from exposed portion 508 than second nearest perimeter 504B of second active material 502B. Likewise, second nearest perimeter 504B of second active material 502B is a greater distance from exposed portion 508 than third nearest perimeter 504C of third active material 502C. In other example, first nearest perimeter 504A of first active material 502A may be a greater distance from exposed portion 508 than second nearest perimeter 504B of second active material 502B and third nearest perimeter 504C of third active material 502C, where second nearest perimeter 504B and third nearest perimeter 504C are substantially the same distance from exposed portion 508 (e.g., where only first nearest perimeter 504A is recessed relative to exposed portion 508).

As noted above, examples of the present disclosure may also include battery assemblies in which the cathode active material of one or more cathode plates is recessed/scalloped relative to an anode tab portion of an anode current collector from an adjacent anode plate within the assembly. FIGS. 12A-12F are conceptual diagrams illustrating an example battery assembly 1100 including cathode plates having an example recessed/scalloped design. Battery assembly 1100 may be substantially the same as all or a portion battery assembly 100 shown, e.g., in FIGS. 4A-5C, and similar features are similarly numbered (e.g., with separator bag 182 of battery assembly 100 shown in FIG. 4A being the same or substantially similar to that of separator bag 1182 of battery assembly 1100 in FIG. 12A.)

Figure 12A:
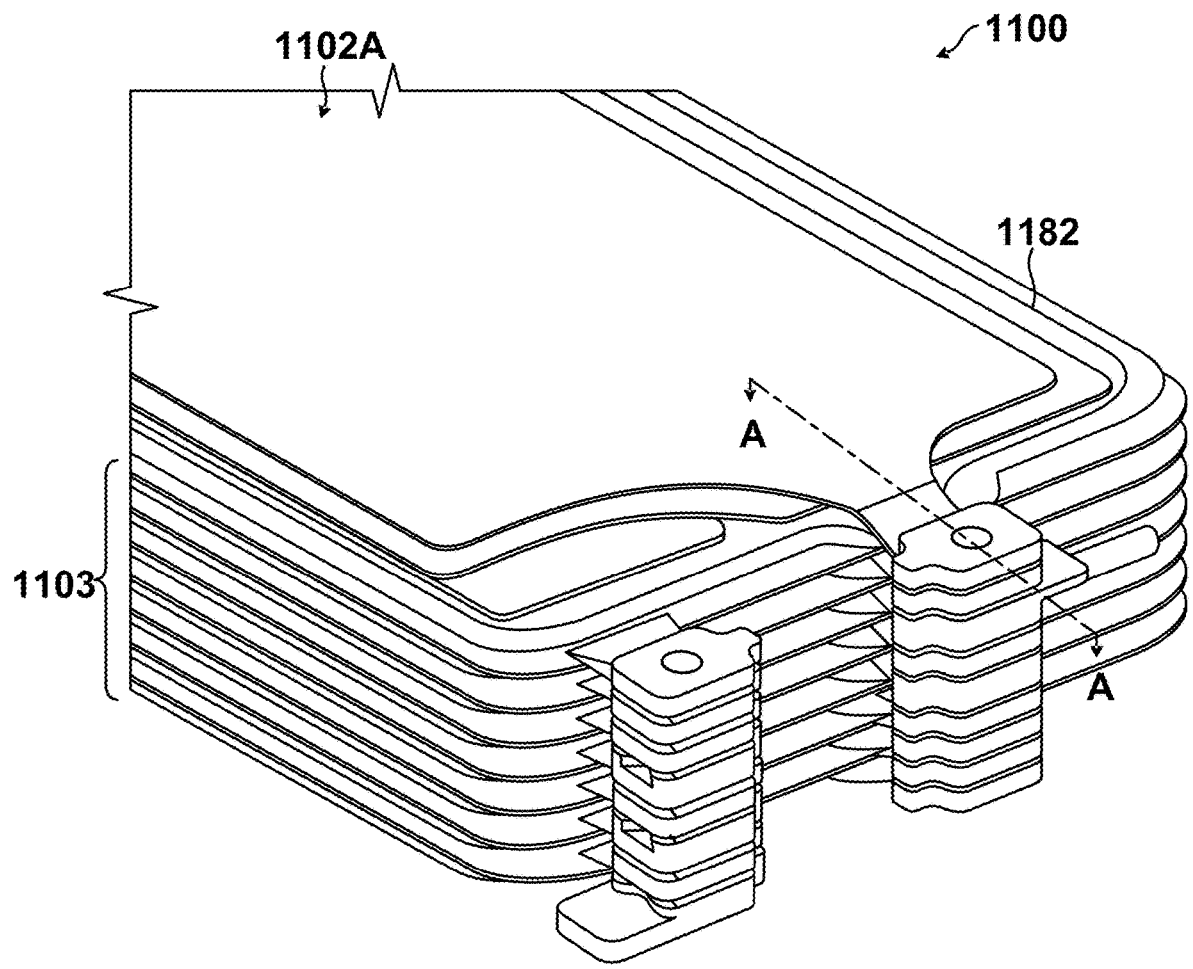
FIGS. 12A-12F are conceptual diagrams illustrating a perspective view of portions of an example battery assembly in accordance with examples of the disclosure.
Figure 12B:
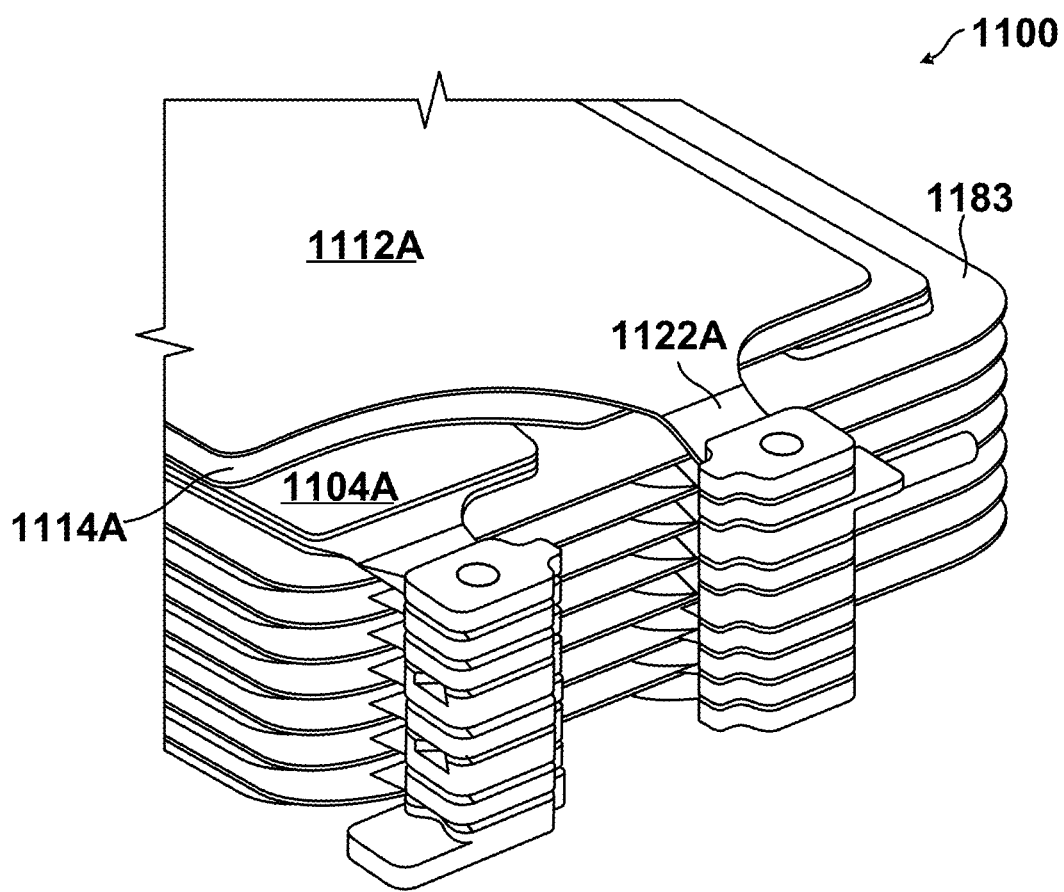

As shown in FIG. 12A, battery assembly 1100 includes electrode stack 1103 with sealed cathode plates (e.g., sealed cathode plate 1104A shown in FIG. 12B) alternating with sealed anode plates (e.g., sealed anode plate 1102A). FIG. 12B shows battery assembly 1100 with separator 1182 removed from sealed anode plate 1102A to reveal anode current collector 1112A and anode active material 1114A. As shown, anode current collector 1112A includes anode tab 1122A extending from the main base of the current collector. As described previously, the current collectors from each anode plate are electrically coupled to each other through respective tabs extending from each current collector out of the separator bags enclosing the base or main portion of the anode current collectors and anode active material. Also shown in FIG. 12B is sealed cathode plate 1104A which includes separator bag 1183 that encloses a portion of the cathode current collector and cathode active material of sealed cathode plate 1104A.

Figure 12C:
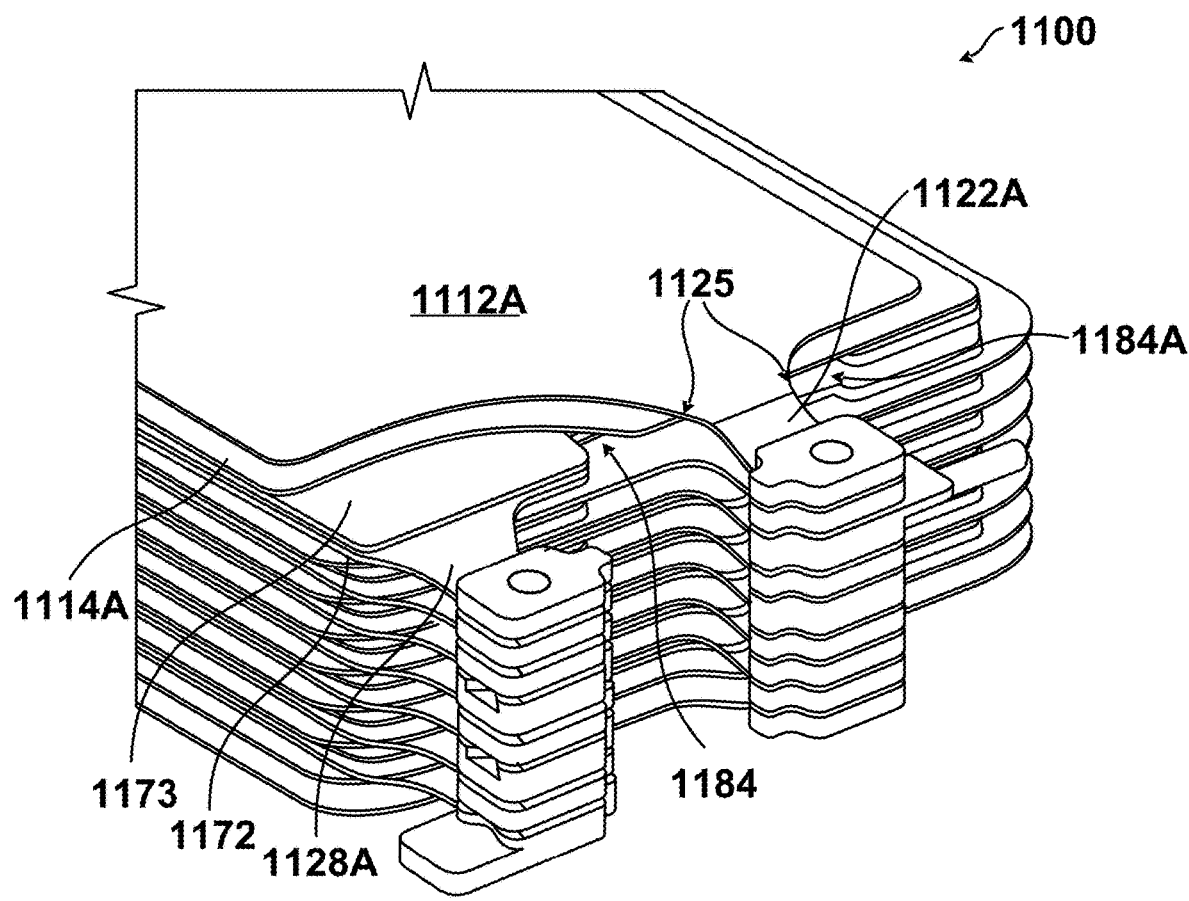

FIG. 12C shows battery assembly 1100 with separator 1183 removed from sealed cathode plate 1104A to reveal cathode current collector 1172 and cathode active material 1173 of sealed cathode plate 1104A. Cathode current collector 1172 include tab 1128A extending from the base or main portion. Like that of the anode, the current collectors from each cathode plate are electrically coupled to each other through respective tabs, such as tab 1128A, extending from each current collector out of the separator enclosures enclosing the base or main portions of the cathode current collectors and cathode active material. In FIG. 12C, portion 1184 of active cathode material 1173 that is recessed/scalloped relative to anode tab 1122A is partially visible. As shown, portion 1184 of active cathode material 1173 and cathode current collector 1172 is recessed relative to anode tab 1122A to increase the distance between the nearest perimeter of active cathode material 1173 relative to edges 1125 of anode tab 1122A of anode current collector 1112A. In this manner, the recessed portion 1184 may allow for a greater amount of expansion of active cathode material 1173 without contact between active cathode material 1173 (and/or separator 1183 enclosing active cathode material 1173) and edges 1152 of anode tab 1122A (and/or exposed portions of anode tab 1122A) during the operating life of battery assembly 1100 (e.g., as compared to instances in which active cathode material 1173 is not recessed as described).

Figure 12D:
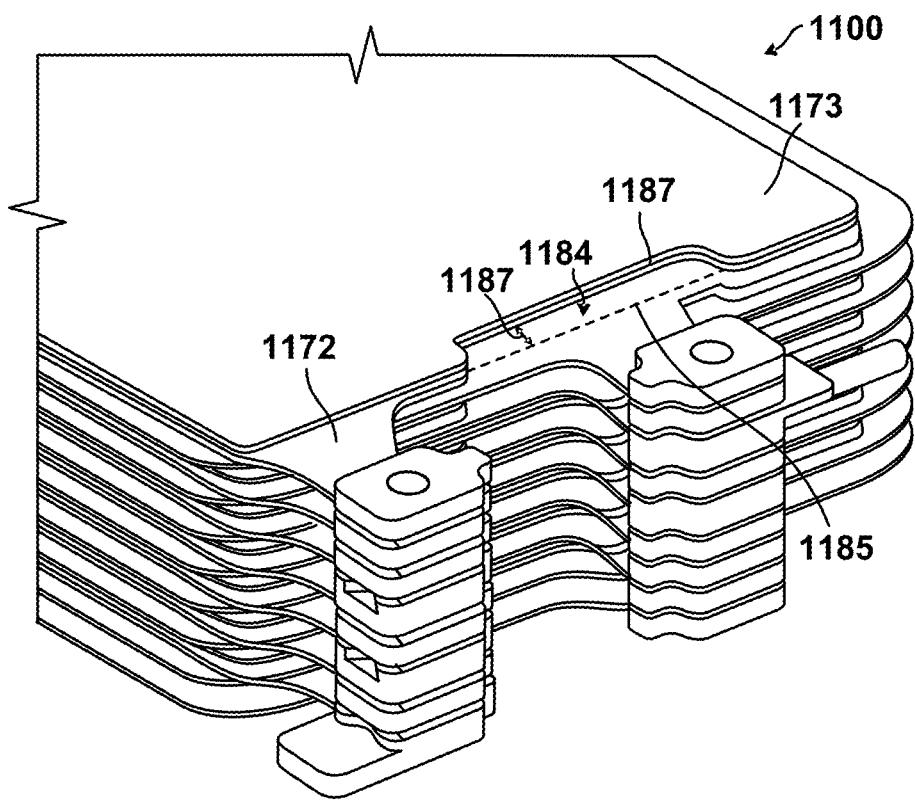

In FIG. 12D, sealed anode plate 1102A is hidden to better illustrate the underlying portions of assembly 1100, such as cathode active material 1173 (in black) and cathode current collector 1172 (in blue), as well as portion 1184 where perimeter 1187 of active cathode material 1173 is recessed/scalloped in accordance with at least some examples of the disclosure. The recessed/scalloped portion 1182 of cathode active material 1173 may allow for a greater distance between perimeter 1186 of cathode active material 1172 and edges 1125 (FIG. 12C) of anode current collector 1112A in the area of tab 1122A. As described above, the increase in distance 1187 between perimeter 1187 and edges 1152 of anode tab 1122A (e.g., compared to a perimeter along dashed line 1185) may allow for expansion of active cathode material 1173, e.g., during the operating life of the battery, without the expansion of active cathode material 1173 causing the overlying separator 1183 and/or active material 1173 itself contacting edge 1125 and/or other portions (e.g., exposed portions) of anode tab 1122A.

Figure 12E:
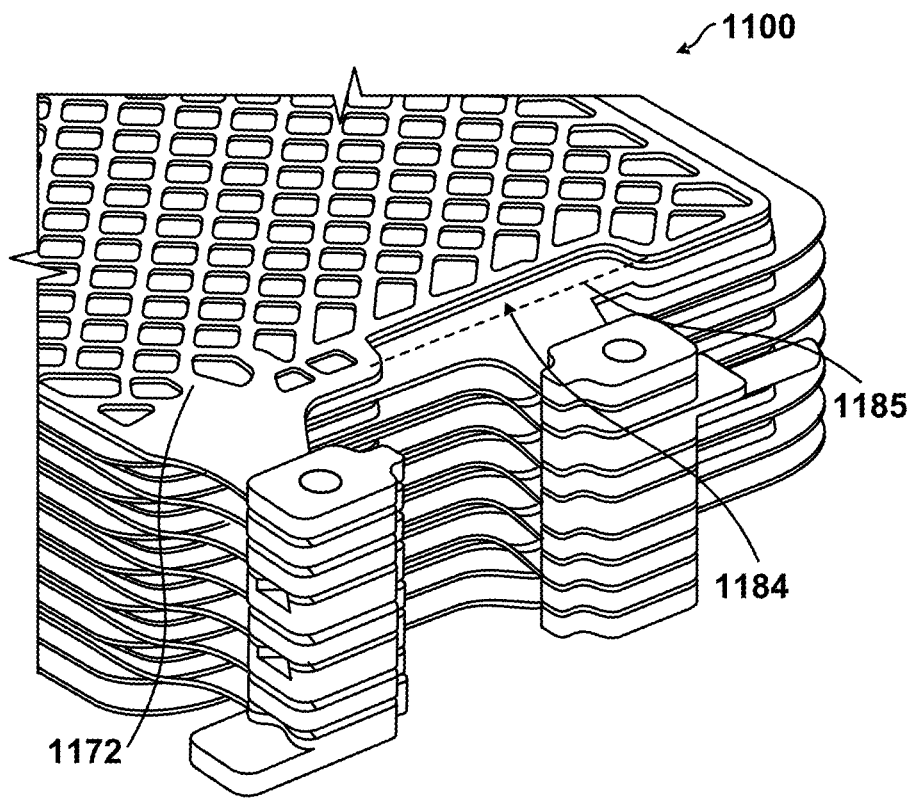
Figure 12F:
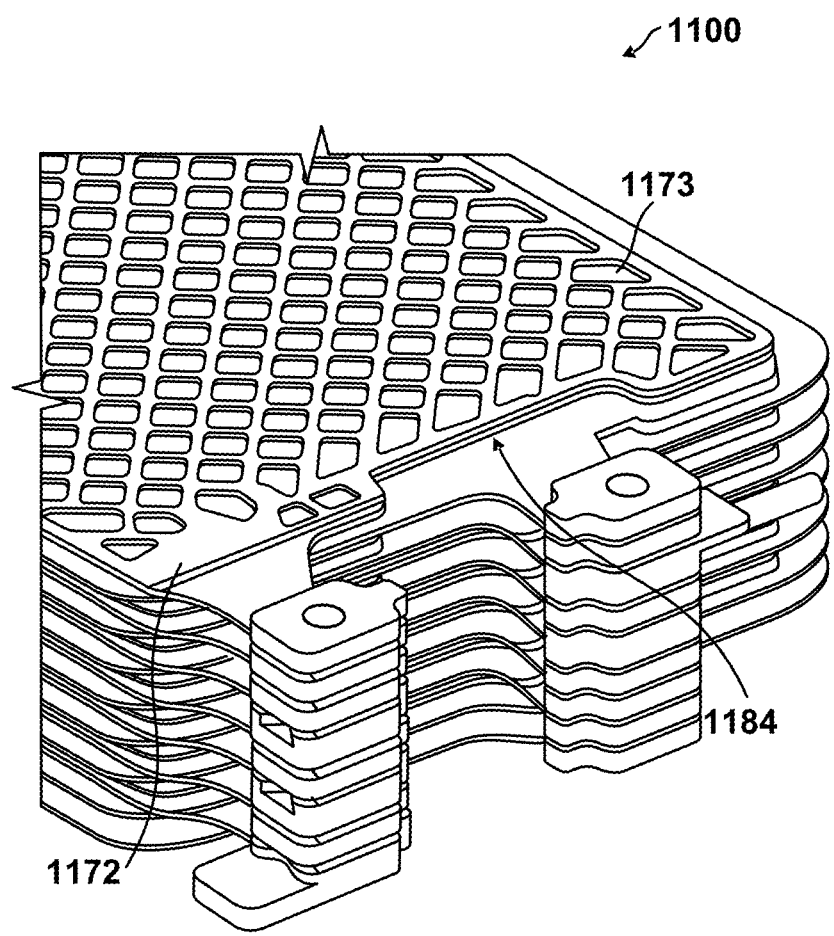

In FIG. 12E, active cathode material 1173 is hidden compared to that shown in FIG. 12D to show cathode current collector 1172. FIG. 12F is similar to FIG. 12E but with active cathode material 1173 being partially transparent to show cathode current collector 1172. As shown, in example assembly 1100, recessed portion 1184 of active cathode material 1173 is achieved by shaping cathode current collector 1172 with a corresponding recess and then depositing active cathode material 1173 to have substantially the same outer perimeter as cathode current collector 1172 including in the area of recessed portion 1184. In some examples, a cathode plate including cathode current collector 1172 with active cathode material 1172 on current collector 1172 may be formed using a die that has a similar recessed profile to that shown in FIGS. 12E and 12F to constrain the active material 1173 to edge/outer perimeter of cathode current collector 1172. Alternatively, a die may be employed to form the active cathode material 1173 to have a "straight" profile (e.g., a profile that follows dashed line 1185 and, subsequently, the active cathode material in the area of recessed/scalloped portion 1184 may be removed by mechanical means to form recessed perimeter 1185 of active material 1173. The same or similar technique may be used to form anode plates with recessed/scalloped active anode material such as those examples described above.

While the example of FIGS. 12A-12H illustrate active material 1173 having an elongated "U" shaped recessed portion 1184, recessed portion 1184 may have any suitable shape and size. For example, recessed portion 1184 may have a shape and size the same or substantially similar to that described herein, e.g., as FIGS. 7A-7D for the recessed active material of an anode plate. In some examples, the recessed perimeter of the active material of the cathode plate(s) may be substantially the same as the perimeter of the underlying cathode current collector so that the cathode current collector may define a recessed portion that is the same or similar to that of the overlaying active cathode material.

Figure 13:
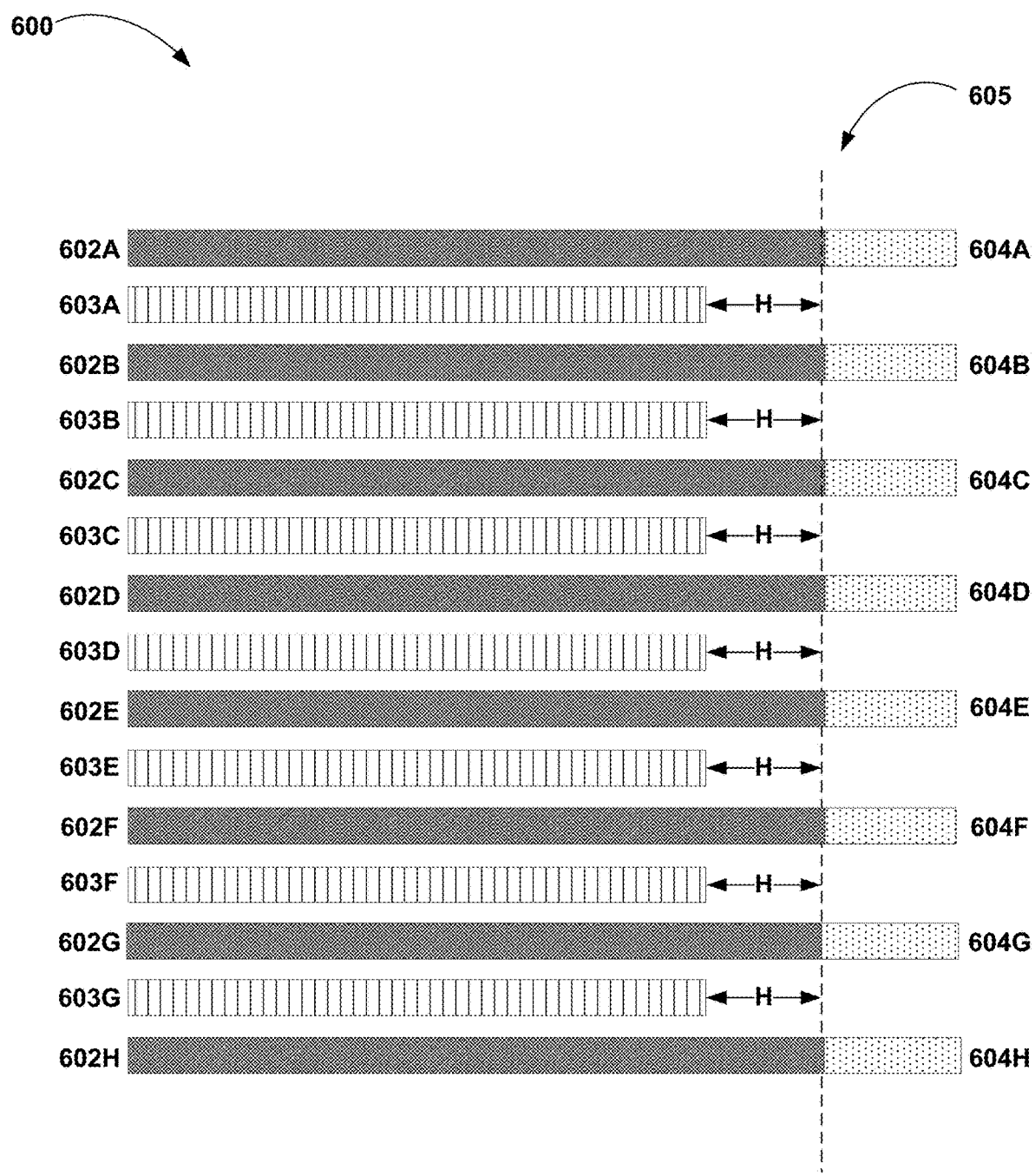
FIG. 13 is a conceptual diagram illustrating cross-sectional views of a portion of an example battery assembly in accordance with examples of the disclosure.

FIG. 13 is a conceptual diagram illustrating cross-sectional views of a portion of an example battery assembly 600 in accordance with some examples of the disclosure. Battery assembly 600 may be substantially similar to that of assembly 1100 shown in FIGS. 12A-12F. FIG. 13 may be representative of a simplified cross-sectional view of assembly 1100 along cross-section A-A shown in FIG. 12A. As will be described, FIG. 13 illustrates an example in which each of the cathode plates include a recessed/scalloped portion of active cathode material, such as that described above for individual sealed cathode plate 1102A.

In the illustrated example, battery assembly 600 comprises first active cathode material 603A to seventh active cathode material 603G. Active cathode materials 603A-603H may be disposed on respective cathode current collectors which are not shown in FIG. 12 for ease of illustration. While individual cathode current collectors may have two layer of active cathode material (e.g., a layer on top and bottom of the current collectors), the active cathode material is shown as single layers for active cathode materials 603A-603H in FIG. 13 for ease of illustration. As such, in some examples, active cathode material 603A is representative of both layers of active cathode material that may be present on the uppermost cathode current collector in the stack shown in FIG. 13, and so forth through 603H. The anode active material and separator portions (e.g., separator bags) of the electrode stack of battery assembly 600 are also not shown in FIG. 13 for ease of illustration.

Battery assembly 600 also includes first anode current collector 602A having tab portion 604A, to eighth current collector 602H having eighth tab portion 604H. In some examples, first anode current collector 602A may correspond to anode current collector 1112A shown, e.g., in FIG. 12B, with first tab portion 604A corresponding to tab 1122A shown, e.g., in FIG. 12B. As previously described with regard to FIGS. 12A-12H, first active cathode material 603A may be recessed relative to tab 606A of first anode current collector 602A, e.g., the edge(s) of tab 604A which may be an exposed portion of first anode current collector 602A. In the example of FIG. 13, a portion of tab 604A (e.g., tab edge(s) 1152) nearest first active cathode material 603A may be represented by dashed line 605 in FIG. 13, with the portion of 604A to the "right" of dashed line 605 being an exposed portion of first anode current collector 602A not covered by a separator and/or not covered by active anode material. The portion of first anode current collector 602A to the "left" of dashed line may be representative of a portion of that is covered by an active anode material and/or a separator.

In some examples, dashed line 605 may be representative of the location of a portion of first anode current collector 602A that has one or more edge portions that may undesirably interact with first active cathode material 603A (and/or overlying separator such as separator 1182) when first active cathode material 603A expands if the nearest perimeter of first active cathode material 603A was not recessed by distance H relative to the location on first anode current collector 602A intersecting with dashed line 605. For example, in an example in which the nearest perimeter of first active cathode material 603A was substantially even with dashed line 605 rather than recessed by distance H, the expansion of first active cathode material 603A during the operating life of battery assembly 600 may cause first active cathode material 603A to contact a portion of tab portion 604A and/or tab portion 604B of the adjacent anode current collectors 602A and 602B (e.g., either directly or by "pushing" an overlying separator such as separator 1182 against tab portion 604A and/or tab portion 604B). By recessing first active cathode material 603A by distance H, such undesired contact may be avoided.

As shown in FIG. 13, each of first active cathode material 603A to seventh active cathode material 603G are recessed by distance H relative to its adjacent anode current collectors in the manner described for first active cathode material 603A. In the example FIG. 13, each of first active cathode material 603A to seventh active cathode material 603G may be recessed by substantially the same distance as each other, e.g., because the expansion of the active cathode material of each cathode plate in battery assembly 600 may be present throughout the electrode stack as compared to the plating of lithium of anode active material which may be greater nearer the top and/or bottom of an electrode stack as described herein. However, examples are not limited to battery assemblies in which the active cathode material for each cathode is recessed/scalloped the same distance. In some examples, the active cathode material for each cathode plate in a battery assembly such as assembly 600 may be recessed/scalloped to some degree but not all being the same distance H. In other examples, the active cathode material of some but not all cathode plates may be recessed/scalloped in a battery assembly such as assembly 600, e.g., with the nearest perimeter of the active cathode material of only some of the cathode plates in the stack being substantially even with dashed line 605.

Figure 14:
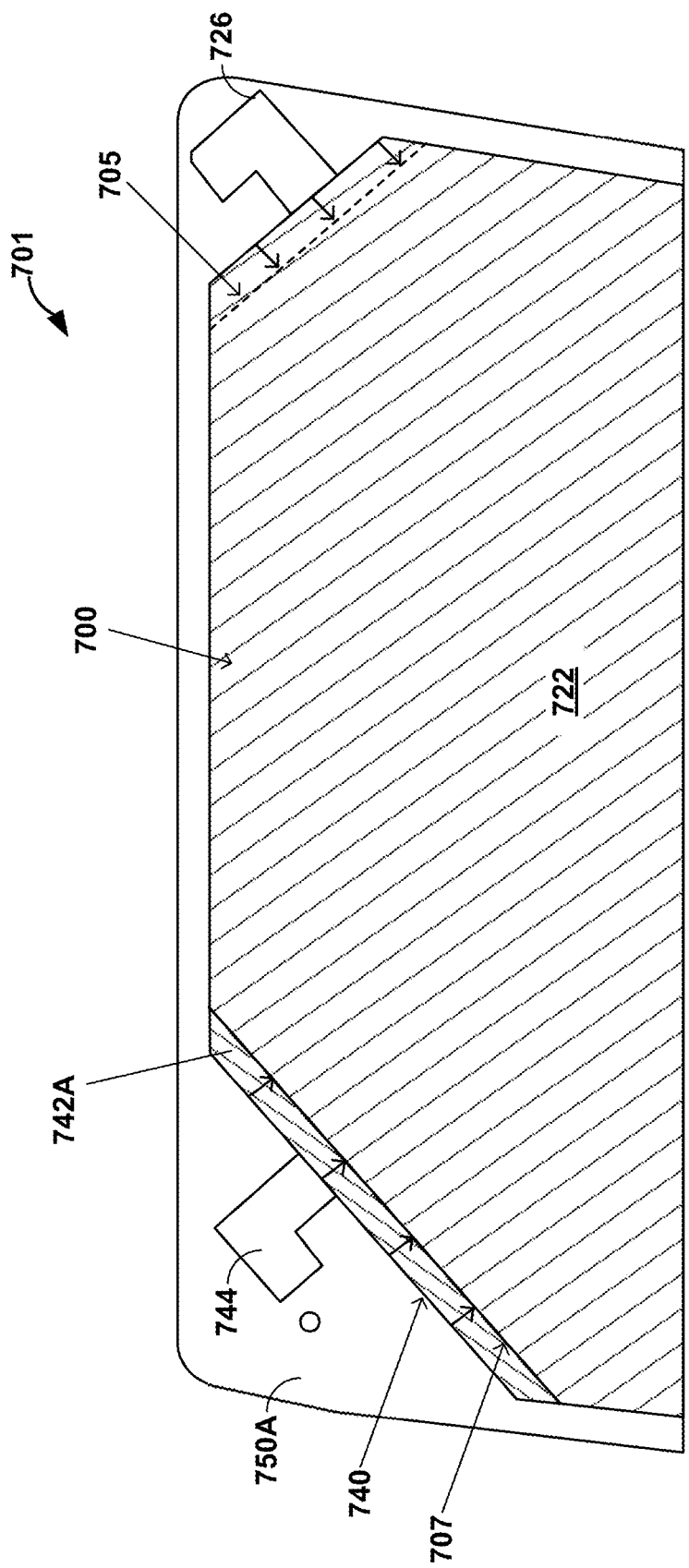
FIG. 14 is a conceptual drawing illustrating a plan view of a portion of an example battery assembly in accordance with examples of the disclosure.

FIG. 14 is a conceptual diagram illustrating another example battery assembly 701 in accordance with examples of the disclosure. In this example, battery assembly 701 includes anode plate 740 and cathode plate 700 stacked on top of bottom housing portion 750A. Cathode plate 700 includes cathode tab 726 and cathode active material 722 covering one or both major surface of a cathode current collector (not shown) in the manner described for previously for other assemblies. Anode plate 740 include anode tab 744 and anode active material 742 covering one or both major surface of anode current collector (not shown) in the manner described for previously for other assemblies. The compositions of anode active material 742 and cathode active material 722 include those materials previously described for other example battery assemblies (e.g., anode active material 742 may include lithium).

Cathode plate 700 is overlaying anode plate 740 in the perspective shown in FIG. 14 so that only a relatively small portion 742a of active material 742 of anode plate 740 directly adjacent to tab 744 is visible. In the example shown in FIG. 14, anode active material 742 includes a portion recessed relative to the exposed portion defined by cathode tab 726 of cathode plate 700. For example, as indicated by the arrows in FIG. 14 next to tab 726, perimeter 705 (indicated by dashed line) of anode active material 742 nearest the exposed portion defined by cathode tab 726 is recessed compared to the perimeter of cathode plate 700 covered with cathode active material 722 directly adjacent to cathode tab 726. Unlike that of some of the earlier describes examples, rather than a curvilinear perimeter at the recessed portion, perimeter 705 of anode active material 742 adjacent to exposed portion of tab 726 follows a substantially linear path, e.g., such that some portions of perimeter 705 of anode active material 742 are further from the exposed portion of tab 726 compared to others. The recess distance indicated by the arrows adjacent to tab 726 and perimeter 705 may be any distance, such as, e.g., at least about 20 mils, at least about 50 mils, at least about 100 mils, such as about 20 mils to about 200 mils, about 50 mils to about 200 mils, or about 100 to about 200 mils. Other values are contemplated.

Cathode active material 722 is similarly recessed relative to the exposed portion defined by anode tab 744 of anode plate 740. For example, perimeter 707 of cathode active material 722 nearest the exposed portion defined by anode tab 744 is recessed compared to the perimeter of anode plate 740 covered with anode active material 742 directly adjacent to anode tab 744. The recess allows for portion 742A of anode active material 742 to be uncovered by cathode active material 722 in the view shown in FIG. 14. Like that of the anode recess, rather than a curvilinear perimeter at the recessed portion, perimeter 707 of cathode active material 722 adjacent to exposed portion of tab 744 follows a substantially linear path, e.g., such that some portions of perimeter 707 of anode active material 742 are further from the exposed portion of tab 726 compared to others. Such a linear perimeter may allow for easier manufacturing compared to that of a curvilinear recess. The recess distance indicated by the arrows adjacent to tab 744 and perimeter 707 may be any distance, such as, e.g., at least about 20 mils, at least about 50 mils, at least about 100 mils, such as about 20 mils to about 200 mils, about 50 mils to about 200 mils, or about 100 to about 200 mils. Other values are contemplated.

In some examples, both the cathode active material and anode active material for battery assembly 701 may be recessed in the manner shown in FIG. 14. In other examples, only the anode material or only the cathode active material may be recessed. By recessing only anode active material 742, advantages as described above may be obtained while any decrease in battery capacity is minimized because the cathode active material 722 is not recessed. Additionally, while assembly 701 is describe with regard to a single anode plate and a single cathode plate, in other example, battery assembly 701 may be multiple cathode plates and/or multiple anode plates, e.g., like the previously describes examples. In the case of multiple anode plates and/or multiple cathode plates, all or a portion of the anode and/or cathode plates may be recessed relative to the exposed portion of the adjacent plates tab in the manner describes herein.

Although not shown, in assembly 701, separator bags may be used to insulate electrically the alternating electrode plates leaving the tabs exposed. For example, cathode plate 700 may be sealed inside a separator bag such that cathode tab 726 is an exposed portion, and anode plate 740 may be sealed inside a separator bag such that anode tab 744 is an exposed portion.

While the examples of the disclosure are primarily described above with regard to a battery assembly having a stacked electrode plate design with more than one cathode plate and more than one anode plate, examples of the disclosure are not limited to such battery assemblies. For example, example electrode assemblies that may have recessed active anode material and/or recessed active cathode material may include battery assemblies with a high rate coiled design, individual stacked plates (e.g., one cathode plate and one anode plate) design, battery assemblies having a jelly roll (wound) configuration, battery assemblies having a "serpentine" configuration (e.g., where there is a weave of lithium between cathode plates), battery assemblies having an "accordion" configuration of single sided electrodes that are "zig-zag" folded in the assembly. U.S. Pat. No. 5,147,737 to Post et al., U.S. Pat. No. 6,933,074 to Frustaci et al., and U.S. Pat. No. 7,592,097 to Urso et al. describe examples of battery assembly configurations which may be modified to include recessed active anode materials and/or recessed active cathode materials in the manner described herein. The entirety of each of the patents are incorporated by reference herein.

As will be apparent from the description above, examples of the present disclosure may provide for one or more benefits. In some examples, a mechanism that can affect high power batteries involves lithium plating that may eventually inhibit electrical isolation between the anode and a cathode tab. In some example, the distance of the cathode tab to the lithium edge that is at the highest temperature has a strong dependency on the time for the active anode material to contact an exposed cathode tab. In a coil design with one tab, the tab can be biased away from the hotter side of the battery to decrease the propensity to lose electrical isolation between anode and cathode. With the current implementation of stacked plate high rate batteries, it may not possible to move the tab. However, it is possible to move the edge of the lithium away from, e.g., the tab closest to the hot side of the battery. While the whole anode could be moved away from the edge of the uninsulated cathode tab, there would be a greater impact on energy density. Recessing/scalloping the lithium near the cathode tab may do two things to positively impact this mechanism. First it may increase the distance that the lithium needs to plate in order for the battery to lose electrical isolation between the active anode material and cathode tab, which may increase the operational life of the battery. Second, it may underbalance the cathode locally. This would put more burden on this edge of the lithium to support its adjacent cathode as well as that cathode material that has not lithium to balance it. As a result, the lithium edge would discharge more quickly than a typical edge. At some larger amount of scalloping, the rate of reduction from discharge could exceed the rate of plating and the net growth of the edge could be zero or always reducing.

As described herein, in some examples, battery assemblies may include a recessed/scalloped lithium (or other anode active material) edge that is adjacent to a cathode tab. This may be applied to high rate coiled designs but it is also applicable to stacked plate high rate batteries. In some examples, the lithium recess/scallop may increase the distance between the anode edge, where lithium plating might occur, to an adjacent cathode tab. It may also imbalance the cathode and should cause additional discharge of the same lithium edge reducing the net rate of plating on that edge.

Various examples have been described in this disclosure. These and other examples are within the scope of the following clauses and claims.

Clause 1. A battery assembly comprising: a first anode plate comprising a first anode current collector and a first active material on the first anode current collector; a second anode plate comprising a second anode current collector and a second active material on the second anode current collector; and a cathode plate between the first anode plate and the second anode plate, wherein the cathode plate comprises a cathode current collector, the cathode current collector having an exposed portion, wherein the first active material is recessed relative to the exposed portion of the cathode plate such that a first nearest perimeter of the first active material is further from the exposed portion of the cathode current collector compared to a second nearest perimeter of the second active material.

Clause 2. The battery assembly of clause 1, wherein the exposed portion is a base of a tab of the cathode current collector.

Clause 3. The battery assembly of any one of clauses 1 or 2, wherein the first nearest perimeter is equidistant from the exposed portion of the cathode current collector.

Clause 4. The battery assembly of any one of clauses 1-3, wherein the first nearest perimeter is asymmetrically curved.

Clause 5. The battery assembly of any one of clauses 1-3, wherein the first nearest perimeter is symmetrically curved.

Clause 6. The battery assembly of any one of clauses 1-3, wherein the first nearest perimeter comprises two edges that are substantially perpendicular to each other.

Clause 7. The battery assembly of any one of clauses 1-6, wherein a first distance between the first nearest perimeter and the exposed portion is at least about 0.6 mm.

Clause 8. The battery assembly of any one of clauses 1-6, wherein a first distance between the first nearest perimeter and the exposed portion is from about 0.6 mm to about 2.5 mm.

Clause 9. The battery assembly of any one of clauses 1-6, wherein a first distance between the first nearest perimeter and the exposed portion is from about 1.0 mm to about 2.0 mm.

Clause 10. The battery assembly of any one of clauses 1-9, wherein the cathode plate comprises a first cathode plate, and the exposed portion comprises a first exposed portion, and the assembly further comprises: a third anode plate, the third anode plate comprising a third anode current collector and a third active material on the third anode current collector; and a second cathode plate between the second anode plate and the third anode plate, wherein the second cathode plate comprises a second cathode current collector, the second cathode current collector having a second exposed portion; wherein the first active material is recessed relative to the first exposed portion of the first cathode plate, and the second active material is recessed relative to the second exposed portion of the second cathode plate.

Clause 11. The battery assembly of clause 10, wherein a first nearest perimeter of the first active material is a first distance from the first exposed portion of the first cathode current collector, a second nearest perimeter of the second active material is a second distance from the second exposed portion of the second cathode current collector, and the first distance and the second distance are substantially the same.

Clause 12. The battery assembly of clause 10, wherein a first nearest perimeter of the first active material is a first distance from the first exposed portion of the first cathode current collector, a second nearest perimeter of the second active material is a second distance from the second exposed portion of the second cathode current collector, and the first distance is greater than the second distance.

Clause 13. The battery assembly of any one of clauses 10-12, wherein the first exposed portion is a first base of a first tab of the first cathode current collector, and the second exposed portion is a second base of a second tab of the second cathode current collector.

Clause 14. The battery assembly of any one of clauses 10-13, further comprising a third cathode plate adjacent the third anode plate, wherein the third cathode plate comprises a third cathode current collector, the third cathode current collector having a third exposed portion; wherein the third active material is recessed relative to the third exposed portion of the third cathode plate.

Clause 15. The battery assembly of clause 14, wherein a first nearest perimeter of the first active material is a first distance from the first exposed portion of the first cathode current collector, a second nearest perimeter of the second active material is a second distance from the second exposed portion of the second cathode current collector, a third nearest perimeter of the third active material is a third distance from the third exposed portion of the third cathode current collector, and the first distance, second distance and third distance are substantially the same.

Clause 16. The battery assembly of clause 14, wherein a first nearest perimeter of the first active material is a first distance from the first exposed portion of the first cathode current collector, a second nearest perimeter of the second active material is a second distance from the second exposed portion of the second cathode current collector, a third nearest perimeter of the third active material is a third distance from the third exposed portion of the third cathode current collector, and the first distance is greater than the second distance, and the second distance is greater than the third distance.

Clause 17. The battery assembly of any one of clauses 14-16, wherein the first exposed portion is a first base of a first tab of the first cathode current collector, the second exposed portion is a second base of a second tab of the second cathode current collector, and the third exposed portion is a third base of a first tab of the third cathode current collector.

Clause 18. A method of forming a battery assembly, the method comprising assembling an electrode stack, the electrode stack comprising: a first anode plate comprising a first anode current collector and a first active material on the first anode current collector; a second anode plate comprising a second anode current collector and a second active material on the second anode current collector; a cathode plate between the first anode plate and the second anode plate, wherein the cathode plate comprises a cathode current collector, the cathode current collector having an exposed portion, wherein the first active material is recessed relative to the exposed portion of the cathode plate such that a first nearest perimeter of the first active material is further from the exposed portion of the cathode current collector compared to a second nearest perimeter of the second active material.

Clause 19. The method of clause 18, wherein assembling the electrode stack comprises stacking the first anode plate, the second anode plate, and the cathode plate between the first anode plate and the second anode plate, and only the exposed portion of the cathode current collector is visible behind the first anode current collector.

Clause 20. The method of any one of clauses 18 or 19, wherein the exposed portion is a base of a tab of the cathode current collector.

Clause 21. The method of any one of clauses 18-20, wherein the first nearest perimeter is equidistant from the exposed portion of the cathode current collector.

Clause 22. The method of any one of clauses 18-21, wherein the first nearest perimeter is asymmetrically curved.

Clause 23. The method of any one of clauses 18-21, wherein the first nearest perimeter is symmetrically curved.

Clause 24. The method of any one of clauses 18-21, wherein the first nearest perimeter comprises two edges that are substantially perpendicular to each other.

Clause 25. The method of any one of clauses 18-24, wherein a first distance between the first nearest perimeter and the exposed portion is at least about 0.6 mm.

Clause 26. The method of any one of clauses 18-24, wherein a first distance between the first nearest perimeter and the exposed portion is from about 0.6 mm to about 2.5 mm.

Clause 27. The method of any one of clauses 18-24, wherein a first distance between the first nearest perimeter and the exposed portion is from about 1.0 mm to about 2.0 mm.

Clause 28. The method of any one of clauses 18-27, wherein the cathode plate comprises a first cathode plate, and the exposed portion comprises a first exposed portion, and the assembly further comprises: a third anode plate, the third anode plate comprising a third anode current collector and a third active material on the third anode current collector; and a second cathode plate between the second anode plate and the third anode plate, wherein the second cathode plate comprises a second cathode current collector, the second cathode current collector having a second exposed portion; wherein the first active material is recessed relative to the first exposed portion of the first cathode plate, and the second active material is recessed relative to the second exposed portion of the second cathode plate.

Clause 29. The method of clause 28, wherein a first nearest perimeter of the first active material is a first distance from the first exposed portion of the first cathode current collector, a second nearest perimeter of the second active material is a second distance from the second exposed portion of the second cathode current collector, and the first distance and the second distance are substantially the same.

Clause 30. The method of clause 28, wherein a first nearest perimeter of the first active material is a first distance from the first exposed portion of the first cathode current collector, a second nearest perimeter of the second active material is a second distance from the second exposed portion of the second cathode current collector, and the first distance is greater than the second distance.

Clause 31. The method of any one of clauses 28-30, wherein the first exposed portion is a first base of a first tab of the first cathode current collector, and the second exposed portion is a second base of a second tab of the second cathode current collector.

Clause 32. The method of any one of clauses 28-31, the assembly further comprising a third cathode plate adjacent the third anode plate, wherein the third cathode plate comprises a third cathode current collector, the third cathode current collector having a third exposed portion; wherein the third active material is recessed relative to the third exposed portion of the third cathode plate.

Clause 33. The method of clause 32, wherein a first nearest perimeter of the first active material is a first distance from the first exposed portion of the first cathode current collector, a second nearest perimeter of the second active material is a second distance from the second exposed portion of the second cathode current collector, a third nearest perimeter of the third active material is a third distance from the third exposed portion of the third cathode current collector, and the first distance, second distance and third distance are substantially the same.

Clause 34. The method of clause 32, wherein a first nearest perimeter of the first active material is a first distance from the first exposed portion of the first cathode current collector, a second nearest perimeter of the second active material is a second distance from the second exposed portion of the second cathode current collector, a third nearest perimeter of the third active material is a third distance from the third exposed portion of the third cathode current collector, and the first distance is greater than the second distance, and the second distance is greater than the third distance.

Clause 35. The method of any one of clauses 28-34, wherein the first exposed portion is a first base of a first tab of the first cathode current collector, the second exposed portion is a second base of a second tab of the second cathode current collector, and the third exposed portion is a third base of a first tab of the third cathode current collector.

Clause 36. An implantable medical device comprising: an outer housing; processing circuitry; and the battery assembly of any one of clauses 1-17 within the outer housing, wherein the processing circuitry is configured to control delivery of electrical therapy from the implantable medical device to a patient using the power supplied by the battery assembly.

Clause 37. A battery assembly comprising: an anode plate comprising an anode current collector and a first active material on the anode current collector, the anode current collector having a tab portion; and a cathode plate adjacent the anode plate, the cathode plate comprising a cathode current collector and second active material, wherein the second active material comprises a recessed portion, the recessed portion being recessed relative to the tab portion of the first anode current collector.

Clause 38. The battery assembly of clause 37, wherein the recessed portion of the second active material is recessed relative to an edge of the tab portion of the first anode current collector.

Clause 39. The battery assembly of clauses 37 or 38, wherein the tab portion comprises an exposed portion of the anode current collector.

Clause 40. The battery assembly of clause 39, wherein the exposed portion of the first anode current collector is a base of the tab portion of the anode current collector.

Clause 41. The battery assembly of clause 37, wherein the anode plate comprises a first anode plate, the anode current collector comprise a first anode current collector, and the tab portion comprises a first tab portion, the assembly further comprising a second anode plate comprising a second anode current collector and these first active material on the second anode current collector, the second anode current collector having a second tab portion, wherein the cathode plate is between the first anode plate and the second anode plate, and wherein the recessed portion of the second active material is recessed relative to the second tab portion of the second anode current collector.

Clause 42. The battery assembly of clause 41, wherein the recessed portion of the second active material of the cathode plate comprises a recessed perimeter, and the recessed perimeter is equidistant from a first exposed portion of the first anode current collector and a second exposed portion of the second anode current collector.

Clause 43. The battery assembly of any one of clauses 37-42, wherein the recessed portion of the second active material comprises a recessed perimeter, and the recessed perimeter is asymmetrically curved.

Clause 44. The battery assembly of any one of clauses 37-42, wherein the recessed portion of the second active material comprises a recessed perimeter, and the recessed perimeter is symmetrically curved.

Clause 45. The battery assembly of any one of clauses 37-42, wherein the recessed portion of the second active material comprises a recessed perimeter, and the recessed perimeter comprises two edges that are substantially perpendicular to each other.

Clause 46. The battery assembly of any one of clauses 37-42, wherein the recessed portion of the second active material comprises a recessed perimeter, and the recessed perimeter comprises three edges forming a substantially rectangular recess along an edge of the cathode current collector.

Clause 47. The battery assembly of any one of clauses 37-46, wherein the recessed portion of the second active material comprises a recessed perimeter, and a distance between the recessed perimeter and the tab portion of the anode current collector is at least about 0.6 mm.

Clause 48. The battery assembly of any one of clauses 37-47, wherein the recessed portion of the second active material comprises a recessed perimeter, and a distance between the recessed perimeter and the tab portion of the anode current collector is from about 0.6 mm to about 2.5 mm.

Clause 49. The battery assembly of clause 37, wherein the cathode plate comprises a first cathode plate, and the cathode current collector comprises a first cathode current collector, and the assembly further comprises: a second anode plate, the second anode plate comprising a second anode current collector and the first active material on the second anode current collector, the second anode current collector having a second tab portion; a third anode plate, the third anode plate comprising a third anode current collector and the first active material on the third anode current collector, the third anode current collector having a third tab portion; and a second cathode plate between the second anode plate and the third anode plate, wherein the second cathode plate comprises the second active material, wherein the first cathode plate is between the first anode plate and the second anode plate, wherein the second active material of the second cathode plates includes a second recessed portion, the second recessed portion being recessed relative to the second tab portion of the second anode current collector.

Clause 50. The battery assembly of clause 49, wherein the recessed portion of the second active material of the first cathode plate is substantially a same as the second recessed portion of the second active material of the second cathode plate.

Clause 51. The battery assembly of clause 49, wherein a distance between a first perimeter of the recessed portion of the second active material of the first cathode plate and the first tab portion of the first anode current collector is substantially a same as a distance between a seconds perimeter of the second recessed portion of the second active material of the second cathode plate and the second tab portion of the second anode current collector.

Clause 52. A method of forming a battery assembly, the method comprising assembling an electrode stack, the electrode stack comprising: a first anode plate comprising a first anode current collector and a first active material on the first anode current collector, the first anode current collector having a first exposed portion; a second anode plate comprising a second anode current collector and a second active material on the second anode current collector, the second anode current collector having a second exposed portion; a cathode plate between the first anode plate and the second anode plate, wherein the cathode plate comprises a cathode current collector, wherein the cathode current collector is recessed relative to the first exposed portion of the first anode current collector and the second exposed portion of the second current collector.

Clause 53. A method comprising forming a battery assembly according to any one of clauses 37-51.

Clause 54. An implantable medical device comprising: an outer housing; processing circuitry; and the battery assembly of any one of clauses 37-51 within the outer housing, wherein the processing circuitry is configured to at least one of control delivery of electrical therapy from the implantable medical device to a patient or sense bioelectrical signals of the patient using power supplied by the battery assembly.

Clause 55. A battery assembly comprising: an anode plate comprising an anode current collector including an anode tab portion, and a first active material on the anode current collector; and a cathode plate comprising a cathode current collector including a cathode tab portion, and a second active material on the cathode current collector, wherein at least one of: the first active material is recessed relative to an exposed portion of the cathode tab portion, or the second active material is recessed relative to the anode tab portion.

Clause 56. The battery assembly of clause 55, wherein the first active material is recessed relative to an exposed portion of the cathode tab portion, and the second active material is recessed relative to the anode tab portion.

The invention claimed is:

1. An assembly comprising:
an anode plate comprising an anode current collector and a first active material on the anode current collector, the anode current collector having a tab portion; and
a cathode plate adjacent the anode plate, the cathode plate comprising a cathode current collector and a second active material,
wherein at least one edge of the second active material defines a recessed portion, the recessed portion being recessed relative to the tab portion of the anode current collector.

2. The assembly of claim 1, wherein the recessed portion of the second active material is recessed relative to an edge of the tab portion of the anode current collector.

3. The assembly of claim 1, wherein the tab portion comprises an exposed portion of the anode current collector.

4. The assembly of claim 3, wherein the exposed portion of the anode current collector is a base of the tab portion of the anode current collector.

5. The assembly of claim 1, wherein the anode plate comprises a first anode plate, the anode current collector comprises a first anode current collector, and the tab portion comprises a first tab portion, the assembly further comprising a second anode plate comprising a second anode current collector and the first active material on the second anode current collector, the second anode current collector having a second tab portion, wherein the cathode plate is between the first anode plate and the second anode plate, and wherein the recessed portion of the second active material is recessed relative to the second tab portion of the second anode current collector.

6. The assembly of claim 5, wherein the recessed portion of the second active material of the cathode plate comprises a recessed perimeter, and the recessed perimeter is equidistant from a first exposed portion of the first anode current collector and a second exposed portion of the second anode current collector.

7. The assembly of claim 1, further comprising an implantable medical device comprising an outer housing and processing circuitry, wherein the anode plate and the cathode plate are within the outer housing, wherein the processing circuitry is configured to control delivery of electrical therapy from the implantable medical device to a patient using the power generated using the anode plate, and the cathode plate.

8. A battery assembly comprising:
an anode plate comprising an anode current collector including an anode tab portion, and a first active material on the anode current collector; and
a cathode plate comprising a cathode current collector including a cathode tab portion, and a second active material on the cathode current collector, wherein at least one of:
the first active material is recessed relative to an exposed portion of the cathode tab portion and relative to an edge of the anode current collector, or
the second active material is recessed relative to the anode tab portion and relative to an edge of the cathode current collector.

9. The battery assembly of claim 8, wherein the first active material is recessed relative to an exposed portion of the cathode tab portion, and the second active material is recessed relative to the anode tab portion.

* * * * *